United States Patent [19]
Fujii

[11] Patent Number: 4,625,555
[45] Date of Patent: Dec. 2, 1986

[54] ULTRASONIC MEASUREMENT METHOD, AND APPARATUS THEREFOR

[75] Inventor: Tadashi Fujii, Fujinomiya, Japan

[73] Assignee: Terumo Kabushiki Kaisha, Tokyo, Japan

[21] Appl. No.: 697,775

[22] Filed: Feb. 4, 1985

[30] Foreign Application Priority Data

Feb. 7, 1984 [JP] Japan ............................ 59-19441

[51] Int. Cl.$^4$ ............................................ G01N 29/04
[52] U.S. Cl. ........................................ 73/597; 73/598; 73/625; 128/660
[58] Field of Search ............... 73/597, 598, 603, 625; 128/660

[56] References Cited

U.S. PATENT DOCUMENTS 3,690,155  9/1972  Eichler .
4,074,564  2/1978  Anderson ............................ 73/596
4,399,702  8/1983  Suzuki ................................ 73/597

FOREIGN PATENT DOCUMENTS 8300009  1/1983  Australia .
8401432  4/1984  Australia .

OTHER PUBLICATIONS

Japanese Language Publication, pp. 292-299 and 482.

Ultrasonic Imaging, an International Journal, vol. 5, No. 2, Apr. 1983, pp. 161 and 168.
Japanese Journal of Medical Ultrasonics, vol. 7, No. 1, 1980, pp. 35-44 by Choi Yong-Soo and Shinichi Matsubara.

Primary Examiner—Howard A. Birmiel
Attorney, Agent, or Firm—Frishauf, Holtz, Goodman & Woodward

[57] ABSTRACT

In a method and apparatus for ultrasonic measurement, there are provided first and second ultrasonic transducers arranged to directly oppose each other across an object interposed therebetween, and a third ultrasonic transducer, the transducers being so arranged that a ray from the third ultrasonic transducer intersects, internally of the object, a ray connecting the first and second ultrasonic transducers. A first period of time required for an ultrasonic wave emitted by the first ultrasonic transducer to be received by the second ultrasonic transducer through the object is measured, as well as second and third periods of time respectively required for an ultrasonic wave emitted by the third ultrasonic transducer to be received by the first and second ultrasonic transducers following scattering of the ultrasonic wave from within the object. Mean propagation velocity of sound or a distribution of propagation velocity of sound internally of the object is measured on the basis of the first, second and third periods of time.

11 Claims, 30 Drawing Figures

ULTRASONIC MEASUREMENT METHOD, AND APPARATUS THEREFOR

BACKGROUND OF THE INVENTION

1. Field of the Invention

This invention relates to a method of performing ultrasonic measurement, and to an apparatus therefor.

2. Description of the Prior Art

One of the systems for ultrasonic measurement in which major advances have been made in recent years is an ultrasound scanner system for medical diagnosis. An apparatus of this type which has come into practical use operates by utilizing a so-called "pulse echo" principle. An ultrasonic pulse is transmitted into a living body and is reflected at a point where the in vivo acoustic impedance is discontinuous. The reflected pulse, namely an echo of the transmitted pulse, is received in the form of an echo signal attenuated to a certain degree owing to the ultrasonic propagation through the living body. The amount of attentuation is corrected by an STC (sensitivity time control) circuit, after which the value of the echo amplitude is subjected to luminance modulation and displayed in the form of a tomograph on a cathode-ray tube by a so-called "B-mode" method. Though the echo signal contains such information as in vivo ultrasonic attenuation and in vivo propagation velocity of sound in addition to the information relating to acoustic impedance, with the B-mode method the in vivo propagation velocity of sound is assumed to be constant and attenuation is corrected for in an arbitrary manner. Consequently, the tomograph obtained is a qualitatively imaged two-dimensional distribution of the in vivo acoustic impedance interface, so that the morphological information relating to the position and shape of biological tissue inevitably forms the core of the information utilized. The state of the art is such that such biological characteristics as degree of attenuation and propagation velocity of sound are not measured, thus making it difficult to perform diversified diagnosis such as, for example, functional diagnosis.

Attempts as measuring propagation velocity of sound in biological tissue by ultrasonic computed tomography (CT) using a transmission method have been reported. See for example the "Japanese Journal of Medical Ultrasonics", vol. 7, No. 1, 1980, pp. 35–44, written by Choi Jong-Soo, and Shinichi Matsubara et al., and "Image Processing for Medical Engineering", edited by Morio Onoe. The principle involved here may be understood from FIG. 1. An ultrasonic probe (i.e. ultrasonic transducer) 10 for transmission emits an ultrasonic pulse 12 which passes through a object (living body) 14 and is received by an ultrasonic probe 16 for reception. The period of time from transmission to reception is measured by utilizing the so-called TOF (time of flight) principle to obtain projection data across the object 14 in a direction parallel to a certain axis. As in X-ray computed tomography, projection data from many different angles are collected over an angular range of 180° relative to the object and the distribution of in vivo propagation velocity of sound is calculated by using a reconstruction algorithm such as a filtered back projection, which is well-known in the art. However, application of this particular method is limited to regions such as the human breast where the ultrasonic waves are capable of being transmitted through the living body over the range of 180°. Application to other regions which include bone or air is not possible in actual practice.

In order to do away with this limitation upon the scope of application, ultrasonic measurement has been attempted by making use of the aforementioned pulse echo prinicple rather than the transmission principle. In a typical arrangement, an ultrasonic pulse is transmitted into a living object from two different directions and a tomograph based on the echo signals is displayed for each direction by the B-mode method. Utilizing the fact that two images may be observed with some shift between them resulting from a refraction phenomenon ascribable to a disparity in propagation velocity of sound, this arrangement attempts to measure the propagation velocity of sound based on the amount of shift that results from a blood vessel or other known object within the object. However, this scheme suffers from major drawbacks such as the need for a known object to be present within the object and the fact that the amount of shift cannot be found unless assumptions are made concerning propagation velocity of sound. The set-up therefore does not truly provide an approach satisfactory for widening application with respect to the human body.

Other methods include a scheme for finding propagation velocity of sound using a cross-beam technique. In this connection, see the *Fifth International Symposium on Ultrasonic Imaging and Tissue Characterization*, "Ultrasonic Imaging", vol. 5, No. 2, April 1983, p. 168. The theory involved will be described with reference to FIG. 2. The set-up includes a ultrasonic probe 18 for transmission directed at the object 14, and two ultrasonic probes 20, 22 for reception arranged at predetermined locations where reflected waves are received in parallel, these directions being different from that in which ultrasonic waves are transmitted by the probe 18. The probe 18 emits an ultrasonic pulse 24 which is scattered by a scatterer 26 inside the object 14. The scattered ultrasonic wave is then received by the ultrasonic probe 20, with the time from pulse emission to reception being designated $T_{18\rightarrow20}$. This period of time is measured. Likewise, an ultrasonic pulse 24 emitted by the probe 18 is scattered by a second scatterer 28 inside the object 14 and the scattered ultrasonic wave is then received by the ultrasonic probe 22, with the time from pulse emission to reception being designated $T_{18\rightarrow22}$. This period of time is also measured. This is followed by computing the difference between the time periods $T_{18\rightarrow20}$, $T_{18\rightarrow22}$, on the basis of which the propagation velocity of sound between the scatterers 26, 28 is found from the following equation:

$$T_{18\rightarrow20}=(x_1/c_1)+(x_2/c_2)$$

$$T_{18\rightarrow22}=(x_1/c_1)+(l/c)+(x_3/c_3)$$

$$T_{18\rightarrow22}-T_{18\rightarrow20}=(l/c)+(x_3/c_3)-(x_2/c_2) \quad (1)$$

where $x_1$, $x_2$, $x_3$, $l$ respectively denote the distance between the ultrasonic probe 18 and the scatterer 26, the distance between the ultrasonic probe 20 and the scatterer 26, the distance between the ultrasonic probe 22 and the scatterer 28, and the distance between the scatterers 26, 28, and $c_1$, $c_2$, $c_3$, $c$ represent the mean propagation velocities of sound across the respective distances. In Eq. (1), $l$ is capable of being measured in advance as the distance between the ultrasonic probes 20, 22 because of the abovementioned parallel conditions under which these probes are arranged. If $(x_3/c_3)-(x_2/c_2)$ on the right side of Eq. (1) is assumed to be zero, then the propagation velocity c of sound may be found from $c=l/(T_{18\rightarrow 22}-T_{18\rightarrow 20})$. However, the assumption holds good only when $x_3/c_3=x_2/c_2$ holds. This means that even if the set-up is such that, e.g., $x_3=x_2$ is established, it will still be necessary to impose the requirement $c_3=c_2$, which runs counter to the intended purpose of actually measuring the propagation velocity of sound. Though the foregoing method is effective in a situation as shown in FIG. 3, in which the propagation velocity of sound of a portion contained in a thin object 32 immersed in a known medium 30 is measured in vitro, it goes without saying that the method is theoretically inapplicable to in vivo situations for the reasons set forth above.

SUMMARY OF THE INVENTION

An object of the present invention is to provide an ultrasonic measurement method and an apparatus therefor whereby propagation velocity of sound inside a object can be measured body rapidly and accurately without processing based on special assumptions and without great limitation as to objects to which application is possible.

Another object of the present invention is to provide an ultrasonic measurement method and an apparatus therefor whereby diversified, highly reliable information having wide application to medical diagnosis and the like can be obtained.

According to one aspect of the present invention, the foregoing objects are attained by providing an ultrasonic measurement method in which first and second ultrasonic transducers are arranged to directly oppose each other across a object interposed therebetween, a third ultrasonic transducer is provided at a predetermined position and directed toward the object, the first, second, and third ultrasonic transducers being so arranged that a ray along a transmission direction of the third ultrasonic transducer intersects, internally of the object, a ray connecting the first and second ultrasonic transducers. The method includes steps of (a) transmitting an ultrasonic wave into the object from the first ultrasonic transducer, (b) measuring a first period of time required for the ultrasonic wave from the first ultrasonic transducer to be received by the second ultrasonic transducer by passing through the object, (c) transmitting an ultransonic wave into the object from the third ultrasonic transducer, (d) measuring second and third periods of time respectively required for the ultrasonic wave from the third ultrasonic transducer to be received by the first and second ultrasonic transducers following scattering of the ultrasonic wave at the intersection of the rays, and (e) measuring mean propagation velocity of sound, on the basis of the first, second and third periods of time, along three ray intervals which are located inside the object and which connect the portion at which the rays intersect and each of the three ultrasonic transducers.

According to another embodiment of the method of the present invention, there is provided an ultrasonic measurement method in which first and second ultrasonic transducers are arranged to directly oppose each other across a object interposed therebetween, a third ultrasonic transducer is provided at a predetermined position and directed toward the object, the first, second, and third ultrasonic transducers being so arranged that a ray along a transmission direction of the third ultrasonic transducer intersects, internally of the object, a ray connecting the first and second ultrasonic transducers. The method includes steps of (a) successively moving the intersection of the rays along a predetermined path of travel in a predetermined plane internally of the object to scan the intersection in the plane while a position of the ray connecting the first and second ultrasonic transducers and a position of the ray along the transmission direction of the third ultrasonic transducer are changed, (b) performing the following steps at each point scanned: ($b_1$) transmitting an ultrasonic wave into the object from the first ultrasonic transducer, ($b_2$) measuring a first period of time required for the ultrasonic wave from the first ultrasonic transducer to be received by the second ultrasonic transducer by passing through the object, ($b_3$) transmitting an ultrasonic wave into the object from the third ultrasonic transducer, and ($b_4$) measuring second and third periods of time respectively required for the ultrasonic wave from the third ultrasonic transducer to be received by the first and second ultrasonic transducers following scattering of the ultrasonic wave at the intersection of the rays, (c) finding propagation velocity of sound between mutually adjacent intersections of the rays at each point scanned in accordance with a predetermined sequence and based on the first, second and third periods of time concerning the mutually adjacent intersections, and (d) successively calculating a distribution of propagation velocity of sound in the plane interiorly of the object based on the propagation velocities of sound found in step (c).

In a modification of the method of the invention, the intersection of the rays is made a focal region of the first, second and third ultrasonic transducers.

In another modification of the method of the invention, a medium of a known propagation velocity of sound is disposed between the object and each of the first, second and third ultrasonic transducers. Here the method includes transmitting an ultrasonic wave toward the object from each of the first, second and third ultrasonic transducers, measuring fourth, fifth and sixth periods of time required for the ultrasonic waves from the first, second and third ultrasonic transducers to be received thereby, respectively, following reflection at object surface points nearest to the ultrasonic transducers, and measuring mean propagation velocity of sound, on the basis of data inclusive of the fourth, fifth and sixth periods of time, along the three ray intervals.

According to another aspect of the present invention, the foregoing objects are attained by providing an ultrasonic measurement apparatus which comprises: first and second ultrasonic transducers arranged to directly oppose each other across a object interposed therebetween; a third ultrasonic transducer provided at a predetermined position and directed toward the object, the first, second, and third ultrasonic transducers being so arranged that a ray along a transmission direction thereof intersects, internally of the object, a ray connecting the first and second ultrasonic transducers; time measuring means for measuring a first period of time required for an ultrasonic wave transmitted by the first ultrasonic transducer to be received by the second ultrasonic transducer by passing through the object, as well as second and third periods of time respectively required for an ultrasonic wave transmitted by the third ultrasonic transducer to be received by the first and second ultrasonic transducers following scattering of the ultasonic wave at the intersection of the rays; and propagation velocity measuring means for measuring mean propagation velocity of sound, on the basis of the first, second and third periods of time measured by the time measuring means, along three ray intervals which are located inside the object and which connect the intersection of the rays and each of the ultrasonic transducers.

In another embodiment of an ultrasonic measurement apparatus according to the present invention, the apparatus comprises: first and second ultrasonic transducers arranged to directly oppose each other across a object interposed therebetween; a third ultrasonic transducer provided at a predetermined position and directed toward the object, the first, second, and third ultrasonic transducers being so arranged that a ray along a transmission direction of the third ultrasonic transducer intersects, internally of the object, a ray connecting the first and second ultrasonic transducers; scanning means for successively moving the intersection of the rays along a predetermined path of travel in a predetermined plane internally of the object to scan the intersection in the plane while a position of the ray connecting the first and second ultrasonic transducers and a position of the ray along the transmission direction of the third ultrasonic transducer are changed; time measuring means for measuring, at each point scanned, a first period of time required for an ultrasonic wave transmitted by the first ultrasonic transducer to be received by the second ultrasonic transducer by passing through the object, as well as second and third periods of time respectively required for an ultrasonic wave transmitted by the third ultrasonic transducer to be received by the first and second ultrasonic transducers following scattering of the ultrasonic wave at the intersection of the rays; and distribution of propagation velocity calculating means for finding propagation velocity of sound between mutually adjacent intersections of the rays at each point scanned in accordance with a predetermined sequence and based on the first, second and third periods of time concerning the mutually adjacent intersections, and for successively calculating a distribution of propagation velocity of sound in the plane interiorly of the object based on the propagation velocities of sound found.

In a modification of the apparatus of the invention, the intersection of the rays is made a focal region of the first, second and third ultrasonic transducers.

In another modification of the apparatus of the invention, the scanning means includes the first, second and third ultrasonic transducers, and circuitry for driving the transducers, wherein each transducer comprises a linear array of electronically scanned ultrasonic transducers.

In yet another modification of the apparatus of the present invention, a medium of a known propagation velocity of sound is disposed between the object and each of the first, second and third ultrasonic transducers, the time measuring means includes means for measuring fourth, fifth and sixth periods of time required for ultrasonic waves transmitted by the first, second and third ultrasonic transducers to be received thereby, respectively, following reflection at object surface points nearest to the ultrasonic transducers, and the propagation velocity of sound measuring means includes means for measuring mean propagation velocity of sound, on the basis of data inclusive of the fourth, fifth and sixth periods of time, along the three ray intervals.

Other features and advantages of the present invention will be apparent from the following description taken in conjunction with the accompanying drawings, in which like reference characters designate the same or similar parts throughout the figures thereof.

DETAILED DESCRIPTION OF THE INVENTION

Basically, the present invention combines the pulse echo and transmission methods and exploits the advantages of both. This makes it possible to measure propagation velocity of sound without requiring projection data 180° around the object, as is necessary in conventional ultrasonic computed tomography. The invention is premised on application of the so-called "ray theory" to sonic propagation just as in ultrasonic computed tomography.

Figure 1:
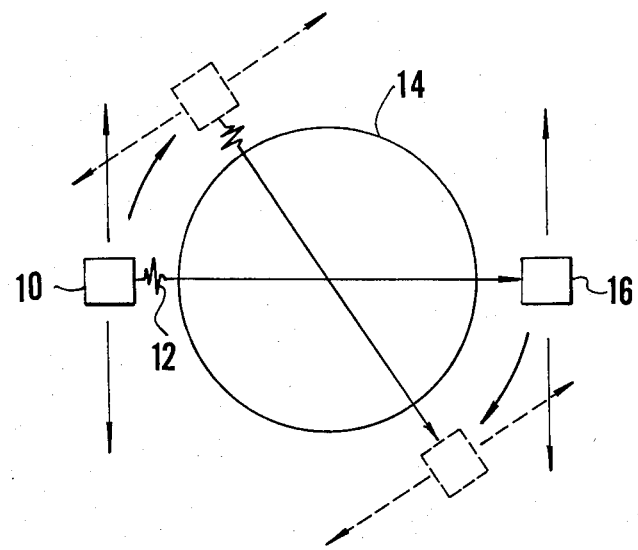
FIG. 1 is a diagrammatic view useful in describing the principle of ultrasonic computed tomography according to the prior art.
Figure 2:
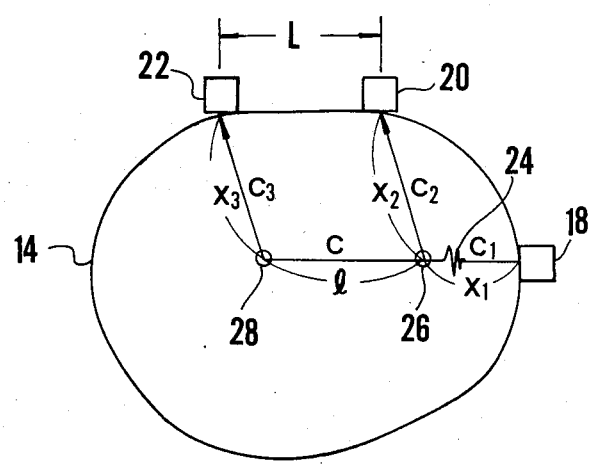
FIG. 2 is a diagrammatic view illustrating an ultrasonic measurement method based on a cross-beam technique according to the prior art.
Figure 3:
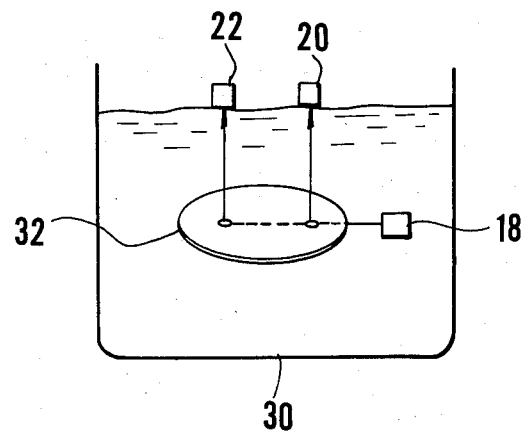
FIG. 3 is a diagrammatic view illustrating an example in which an ultrasonic measurement is performed by employing the cross-beam technique.
Figure 4:
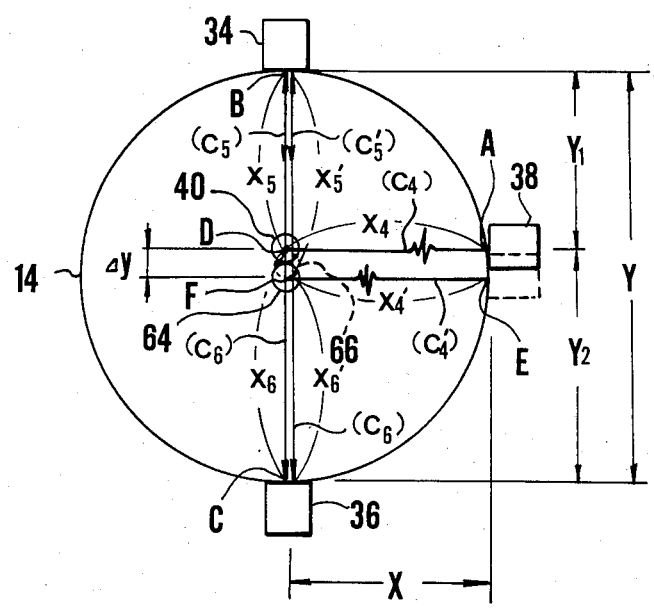
FIG. 4 is a diagrammatic view useful in describing the principle of the present invention in a case where ultrasonic probes (which equals ultrasonic transducers hereinafter except otherwise specified are brought into contact with a object under examination.

FIG. 4 is a diagrammatic view useful in describing the principle of the present invention. An ultrasonic probe 34 for both transmission and reception and an ultrasonic probe 36 for reception are set up to directly oppose each other across an object 14 interposed therebetween. Another ultrasonic probe 38 for transmission is directed toward the object 14 and provided at a predetermined position which is not located on the straight line connecting the ultrasonic probes 34, 36. These ultrasonic probes are able to transmit and receive ultrasonic pulses, and are called ultrasonic transducers rather than ultrasonic probes. So, the term ultrasonic probe equals ultrasonic transducer except as otherwise specified. As shown in FIG. 4, the three ultrasonic probes 34, 36, 38 are brought into direct acoustic contact with the object 14 and are so arranged that the ray connecting the ultrasonic probes 34, 36 and the ray along the transmission direction of the ultrasonic probe 38 intersect.

Let A, B and C represent the positions of the three ultrasonic probes 38, 34, 36, respectively, and let D represent the position of the center of a scatterer 40 residing at the portion of the object 14 where the aforementioned rays intersect. Further, let $x_4$, $x_5$, $x_6$ denote distances AD, BD, CD, respectively, and let $c_4$, $c_5$, $c_6$ designate the mean sonic velocities of ultrasonic pulses propagated along these distances, respectively. Also, let Y be the distance between the ultrasonic probes 34, 36, and X the distance between the ultrasonic probe 38 and the straight line connecting the points B and C.

When an ultrasonic wave is transmitted into the object 14 from the ultrasonic probe 38, the wave is scattered by the scatterer 40. Let the propagation times from emission of the ultrasonic wave from the probe 38 to reception of the ultrasonic wave by the probes 34, 36 following scattering be represented by $T_{34}^{38}$, $T_{36}^{38}$, respectively. $T_{34}^{38}$, $T_{36}^{38}$ will then be expressed as follows:

$$T_{34}^{38} = (x_4/c_4) + (x_5/c_5) \quad (2)$$

$$T_{36}^{38} = (x_4/c_4) + (x_6/c_6) \quad (3)$$

Finding the difference between these two periods of time results in the following equation:

$$T_{36}^{38} - T_{34}^{38} = (x_6/c_6) - (x_5/c_5) \quad (4)$$

Next, let $T_{36}^{34}$ represent the propagation time from emission of an ultrasonic wave from the ultrasonic probe 34 to reception of the ultrasonic wave by the ultrasonic probe 36, the ultrasonic wave passing completely through the object 14. This propagation time is expressed as follows:

$$T_{36}^{34} = (x_5/c_5) + (x_6/c_6) \quad (5)$$

From Eqs. (4), (5) we have $$(x_6/c_6) = \tfrac{1}{2}[(T_{36}^{38} - T_{34}^{38}) + T_{36}^{34}] \quad (6)$$

$$(x_5/c_5) = -\tfrac{1}{2}[(T_{36}^{38} - T_{34}^{38}) - T_{36}^{34}] \quad (7)$$

Owing to the positional relationship among the ultrasonic probes 34, 36, 38, we may write $x_5 = Y_1$, $x_6 = Y_2$. Therefore, $c_5$, $c_6$ can be found from Eqs. (6), (7):

$$c_6 = 2Y_2/[T_{36}^{34} + T_{36}^{38} - T_{34}^{38}] \quad (8)$$

$$c_5 = 2Y_1/[T_{36}^{34} - T_{36}^{38} + T_{34}^{38}] \quad (9)$$

Similarly, we can derive the following from Eqs. (7) and (2) or from Eqs. (6) and (3):

$$(x_4/c_4) = T_{34}^{38} + \tfrac{1}{2}[(T_{36}^{38} - T_{34}^{38}) - T_{36}^{34}] \quad (10)$$

or $$(x_4/c_4) = T_{36}^{38} - \tfrac{1}{2}[(T_{36}^{38} - T_{34}^{38}) + T_{36}^{34}] \quad (11)$$

Since we may write X for $x_4$, $c_4$ can be obtained from Eqs. (10), (11) as follows:

$$c_4 = 2X/[-T_{36}^{34} + T_{36}^{38} + T_{34}^{38}] \quad (12)$$

It is thus possible to measure all of the pertinent mean propagation velocities $c_4$, $c_5$, $c_6$ of sound along the propagation paths of the ultrasonic waves which traverse the three ray intervals or legs connecting the scatterer 40 with each of the ultrasonic probes 38, 34, 36, respectively, inside the object 14. It should be noted that the aforementioned TOF method conventionally applied in ultrasonic computed tomography may be utilized to measure the propagation time period $T_{36}^{34}$. The propagation time periods $T_{34}^{38}$, $T_{36}^{38}$ are measured in a manner which will now be described.

Figure 5:
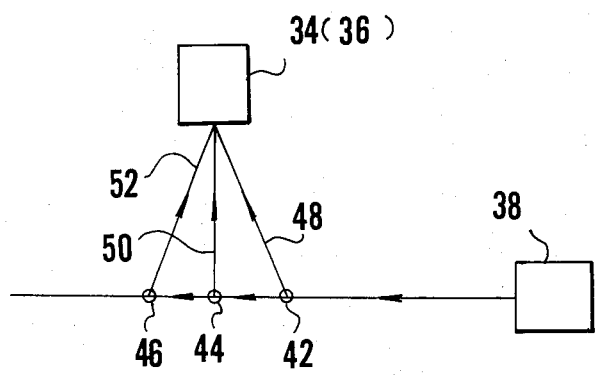
FIGS. 5 through 8 are explanatory view illustrating a method of measuring propagation time of a scattered ultrasonic wave.
Figure 6:
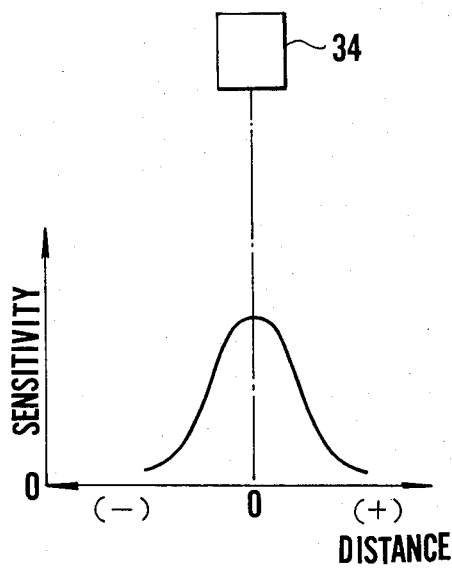
Figure 7:
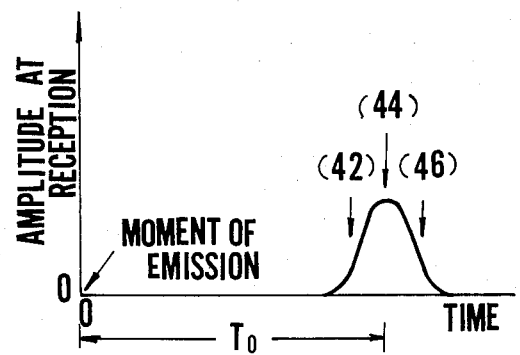

As shown in FIG. 5, assume that three scatterers 42, 44, 46 reside within the range of directivity of the ultrasonic probe 34 or 36. An ultrasonic pulse emitted by the ultrasonic probe 38 is scattered by each of the three scatterers 42, 44, 46 in succession and is received by probe 34 or 36 along three paths 48, 50, 52 one after another. If the propagation velocity of sound along each propagation path differs slightly from that along the other paths, the period of time required for propagation will be proportional to the propagation distance. The scattered pulses will therefore reach the ultrasonic probe 34 or 36 first along path 48, then along path 50, and finally along path 52. If the directivity or sensitivity of the ultrasonic probe 34 or 36 forms a Gaussian distribution as shown for example in FIG. 6 in which the sensitivity is highest on the central axis of the probe, then the amplitude of the ultrasonic wave received from the scatterer 44 along the path 50 will be the largest of the three (see FIG. 7). Accordingly, it will suffice to detect the instant at which the amplitude of the received wave attains a maximum value and treat this instant as the time at which the ultrasonic pulse scattered by the scatterer 44 is received. In FIG. 7, $T_0$ is either $T_{34}^{38}$ or $T_{36}^{38}$. The precision at which $T_{34}^{38}$, $T_{36}^{38}$ are measured can be raised by sharpening the directivity of the ultrasonic probes 34, 36, 38. This may be achieved by making small the region where the directivities cross, as shown by the hatched portion in FIG. 8.

Figure 9:
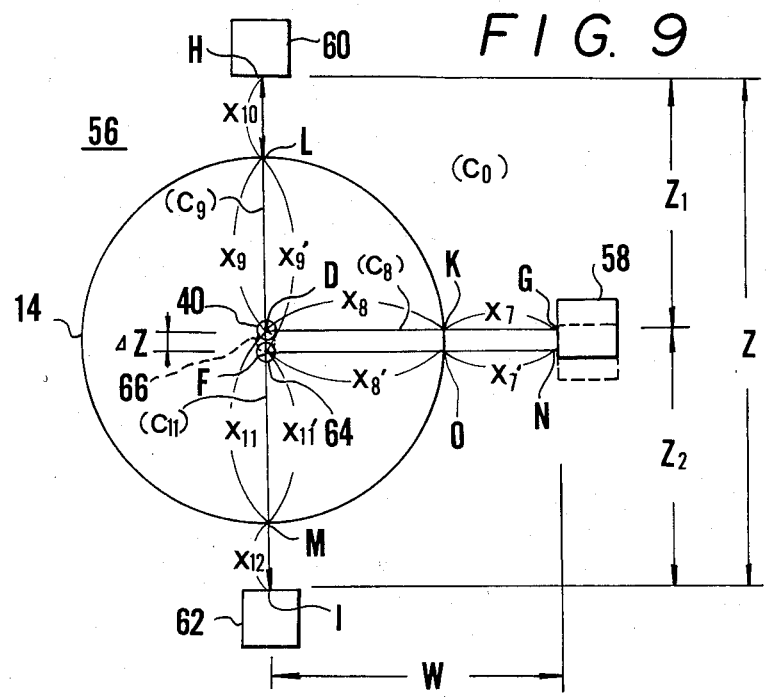
FIG. 9 is a diagrammatic explanatory view illustrating the principle of the present invention in a case where a known medium is disposed between the object and each of the ultrasonic probes.

Reference will now be had to FIG. 9 to describe a mean velocity measurement principle for an arrangement where the ultrasonic probes, rather than being in direct contact with the object, are spaced away from the object across an intervening medium (such as water) in which the velocity of sound is known. As shown in FIG. 9, the object 14 and ultrasonic probes 58, 60, 62, each of which is capable of both transmission and reception, are placed in a predetermined positional relationship, with degased water 56 being disposed between the object and the probes. Let G, H and I represent the positions of the three ultrasonic probes 58, 60, 62, respectively, and let D represent the position of the center of a scatterer 40 residing at the portion of the object 14 where the rays intersect. Further, let K, L, M represent the points at which the rays of the probes 58, 60, 62 intersect the surface of the object 14, respectively, and let $x_7$, $x_8$, $x_9$, $x_{10}$, $x_{11}$, $x_{12}$ denote distances GK, KD, DL, LH, DM, MI, respectively. Let $c_8$, $c_9$, $c_{11}$ designate the mean propagation velocities of ultrasonic pulses propagated along the paths KD, DL, DM, respectively, and let $c_0$ be the mean propagation velocity of sound in the degased water 56. Also, let Z be the distance between the opposed ultrasonic probes 60, 62, and W the distance between the scatterer 40 and the ultrasonic probe 58.

Let $T_{60}^{58}$, $T_{62}^{58}$ represent the propagation times required for an ultrasonic pulse, which is transmitted toward the object 14 by the ultrasonic probe 58, to reach the ultrasonic probes 60, 62 following scattering at the scatterer 40, respectively. $T_{60}^{58}$, $T_{62}^{58}$ will be expressed as follows:

$$T_{60}^{58} = (x_7/c_0) + (x_8/c_8) + (x_9/c_9) + (x_{10}/c_0) \quad (13)$$

$$T_{62}^{58} = (x_7/c_0) + (x_8/c_8) + (x_{11}/c_{11}) + (x_{12}/c_0) \quad (14)$$

Finding the difference between these two periods of time results in the following equation:

$$T_{62}^{58} - T_{60}^{58} = (x_{11}/c_{11}) - (x_9/c_9) + (x_{12}/c_0) + (x_{10}/c_0) \quad (15)$$

Next, let $T_{62}^{60}$ represent the propagation time required for an ultrasonic pulse emitted from the ultrasonic probe 60 to reach the ultrasonic probe 62 by passing through the object 14. This propagation time is expressed as follows:

$$T_{62}^{60} = (x_{10}/c_0) + (x_9/c_9) + (x_{11}/c_{11}) + (x_{12}/c_0) \quad (16)$$

Further, let $T_{60}^{60}$ represent the propagation time required for an ultrasonic pulse emitted from the ultrasonic probe 60 to be received in the form of a reflected wave by the same probe 60 following reflection at the point L on the surface of the object 14. This propagation time period is represented by the following:

$$T_{60}^{60} = 2(x_{10}/c_0) \quad (17)$$

Likewise, propagation time periods $T_{58}^{58}$, $T_{62}^{62}$ from emission of ultrasonic pulses by the ultrasonic probes 58, 62 until their reception of the reflected waves from the points K, M on the object surface, respectively, are expressed by the following:

$$T_{58}^{58} = 2 \cdot (x_7/c_0) \quad (18)$$

$$T_{62}^{62} = 2 \cdot (x_{12}/c_0) \quad (19)$$

Taking the difference between Eqs. (15) and (16) gives us the following equation:

$$(T_{62}^{58} - T_{60}^{58}) - T_{62}^{60} = -2 \cdot (x_9/c_9) - 2 \cdot (x_{10}/c_0) \quad (20)$$

and we obtain the following from Eqs. (17), (20):

$$c_9 = 2x_9 / [T_{62}^{60} - (T_{62}^{58} - T_{60}^{58} - T_{60}^{58} + T_{60}^{60})] \quad (21)$$

Since $Z_1 = x_9 + x_{10}$ is given, we may obtain $x_9$ from Eq. (17) by way of the following equation:

$$x_9 = Z_1 - (T_{60}^{60} \cdot c_0)/2 \quad (22)$$

Since $c_0$ and $Z_1$ are known and $T_{60}^{60}$ is a measurable quantity, $x_9$ can be calculated and Eqs. (21), (22) provide an equation for calculating $c_9$. Specifically, we may write $$c_9 = [2Z_1 - (T_{60}^{60} \cdot c_0)] / [T_{62}^{60} - T_{62}^{58} + T_{60}^{58} - T_{60}^{60}] \quad (23)$$

Taking the sum of Eqs. (15), (16), we have:

$$(T_{62}^{58} - T_{60}^{58}) + T_{62}^{60} = 2 \cdot (x_{11}/c_{11}) + 2 \cdot (x_{12}/c_0) \quad (24)$$

From Eqs. (19), (24) we obtain the following:

$$2 \cdot (x_{11}/c_{11}) = (T_{62}^{58} - T_{60}^{58}) + T_{62}^{60} - T_{62}^{62} \quad (25)$$

Since $Z_2 = x_{11} + x_{12}$ is given, $x_{11}$ is obtained from Eq. (19) by using the following equation:

$$x_{11} = Z_2 - (T_{62}^{62} \cdot c_0)/2 \quad (26)$$

and $c_{11}$ may be calculated from Eqs. (25), (26) in accordance with the following:

$$c_{11} = [2Z_2 - (T_{62}^{62} \cdot c_0)] / [T_{62}^{60} + T_{62}^{58} - T_{60}^{58} - T_{62}^{62}] \quad (27)$$

To find $c_8$, the following is derived from Eqs. (13), (17) and (20):

$$(x_8/c_8) = T_{60}^{58} - (x_7/c_0) - (\tfrac{1}{2}) \cdot [(T_{62}^{58} - T_{60}^{58}) - T_{62}^{60}] + (3/2) \cdot T_{60}^{60} \quad (28)$$

Since the relation $W = x_7 + x_8$ is given, $c_8$ is obtained from Eqs. (18), (28) by using the following equation:

$$c_8 = 2[W - T_{58}^{58} \cdot c_0] / [T_{62}^{60} - T_{62}^{58} + 3 \cdot T_{60}^{58} + 3 \cdot T_{60}^{60} - T_{58}^{58}] \quad (29)$$

Thus, just as in the arrangement of FIG. 4, the pertinent mean propagation velocities $c_8$, $c_9$, $c_{11}$ of sound along the three ray intervals or legs connecting the scatterer 40 with each of the ultrasonic probes inside the object 14 can be calculated.

The foregoing discussion of the principle of the present invention suggests that by using three ultrasonic probes and combining the pulse echo and transmission methods, propagation velocity of sound in a object can be measured without accumulating projection data 180° about the periphery of the region of interest, as is necessary in ultrasonic computed tomography according to the prior art.

We shall now describe a method of obtaining a distribution of propagation velocity of sound for the entirety of a object.

Let us return to FIG. 4 for a dicussion of the fundamental principle. Let $t_4$, $t_5$, $t_6$ represent the periods of time needed for an ultrasonic pulse to propagate across the intervals $x_4$, $x_5$, $x_6$, respectively, when the ultrasonic probe 38 is situated at the point A. We may then write $$T_{34}^{38}(A) = t_4 + t_5 \qquad (30)$$

$$T_{36}^{38}(A) = t_4 + t_6 \qquad (31)$$

$$T_{36}^{34} = t_5 + t_6 \qquad (31)$$

where $T_{34}^{38}(A)$, $T_{36}^{38}(A)$ are the times required for an ultrasonic pulse emitted by the ultrasonic probe 38 at the point A to be received by the ultrasonic probes 34, 36, respectively, following scattering at the scatterer 40. The time periods $t_5$, $t_6$ may be written as follows from the three equations (30), (31), (32):

$$t_5 = [T_{34}^{38}(A) + T_{36}^{34} - T_{36}^{38}(A)]/2 \qquad (33)$$

$$t_6 = [T_{36}^{38}(A) + T_{36}^{34} - T_{34}^{38}(A)]/2 \qquad (34)$$

The ultrasonic probe 38 is then moved a distance $\Delta y$ in the Y direction to place it at a point E, with the portion of the object 14 at which the rays intersect now being a scatterer 64. Under these circumstances, let F represent the center of the scatterer 64, and let $t'_4$, $t'_5$, $t'_6$ be the times needed for an ultrasonic pulse to propagate across intervals $x'_4$, $x'_5$, $x'_6$, respectively. We may therefore obtain $t'_5$, $t'_6$ in a manner similar to that described above, giving us the following:

$$t'_5 = [T_{34}^{38}(E) + T_{36}^{34} - T_{36}^{38}(E)]/2 \qquad (35)$$

$$t'_6 = [T_{36}^{38}(E) + T_{36}^{34} - T_{34}^{38}(E)]/2 \qquad (36)$$

A very small zone 66 surrounded by the broken line in FIG. 4 is defined between the scatterers 40, 64. Using Eqs. (33), (35) or (34), (36), we may calculate the propagation velocity c of sound in the zone 66 as follows:

$$c = \Delta y/(t'_5 - t_5) \qquad (37)$$
$$= 2\Delta y/[T_{34}^{38}(E) - T_{36}^{38}(E) - T_{34}^{38}(A) + T_{36}^{38}(A)]$$

or $$c = \Delta y/(t_6 - t'_6) \qquad (38)$$
$$= 2\Delta y/[T_{36}^{38}(A) - T_{34}^{38}(A) - T_{36}^{38}(E) + T_{34}^{38}(E)]$$

For the arrangement shown in FIG. 9, let $t_7$, $t_8$, $t_{11}$, $t_{12}$ represent the periods of time needed for an ultrasonic pulse to propagate across the respective intervals $x_7$, $x_8$, $x_{11}$, $x_{12}$ when the ultrasonic probe 58 is situated at the point G. Then let the ultrasonic probe 58 be moved from the point G a distance $\Delta z$ in the Z direction to place it at a point N, with the center of the scatterer 64 being designated F as before. Under these circumstances, let $t'_7$, $t'_8$, $t'_{11}$, $t'_{12}$ be the times needed for an ultrasonic pulse to propagate across intervals $x'_7$, $x'_8$, $x'_{11}$, $x_{12}$, respectively. We may therefore obtain the following:

$$T_{60}^{58}(G) = t_7 + t_8 + t_9 + t_{10} \qquad (39)$$

$$T_{62}^{58}(G) = t_7 + t_8 + t_{11} + t_{12} \qquad (40)$$

$$T_{60}^{58}(N) = t'_7 + t'_8 + t'_9 + t_{10} \qquad (41)$$

$$T_{62}^{58}(N) = t'_7 + t'_8 + t'_{11} + t_{12} \qquad (42)$$

$$\left. \begin{array}{l} T_{62}^{60} = t_9 + t_{10} + t_{11} + t_{12} \\ = t'_9 + t_{10} + t'_{11} + t_{12} \end{array} \right\} \qquad (43)$$

From Eqs. (39), (40), (43) we obtain the following equations:

$$t_9 + t_{10} = [T_{60}^{58}(G) + T_{62}^{60} - T_{62}^{58}(G)]/2 \qquad (44)$$

$$t_{11} + t_{12} = [T_{62}^{58}(G) + T_{62}^{60} - T_{60}^{58}(G)]/2 \qquad (45)$$

From eqs. (41), (42), (43) we obtain:

$$t'_9 + t_{10} = [T_{60}^{58}(N) + T_{62}^{60} - T_{62}^{58}(N)]/2 \qquad (46)$$

$$t'_{11} + t_{12} = [T_{62}^{58}(N) + T_{62}^{60} - T_{60}^{58}(N)]/2 \qquad (47)$$

Using Eqs. (44), (46) or (45), (47), we may calculate the propagation velocity c of sound in the very small zone 66 between the scatterers 40, 64 in FIG. 9 as follows:

$$c = \Delta z/[(t'_9 + t_{10}) - (t_9 + t_{10})] \qquad (48)$$
$$= 2\Delta z/[T_{60}^{58}(N) - T_{62}^{58}(N) - T_{60}^{58}(G) + T_{62}^{58}(G)]$$

or $$c = \Delta z/[(t'_{11} + t_{12}) - (t_{11} + t_{12})] \qquad (49)$$
$$= 2\Delta z/[T_{62}^{58}(N) - T_{60}^{58}(N) - T_{62}^{58}(G) + T_{60}^{58}(G)]$$

Figure 10:
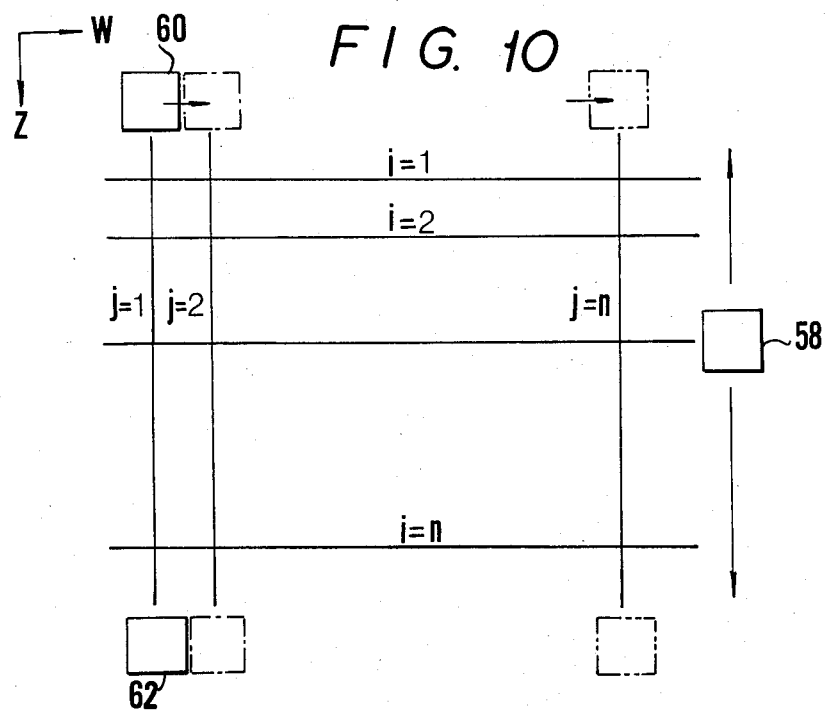
FIG. 10 is a view useful in describing the operation of the present invention and illustrates the manner in which ultrasonic probes are made to scan.
Figure 11:
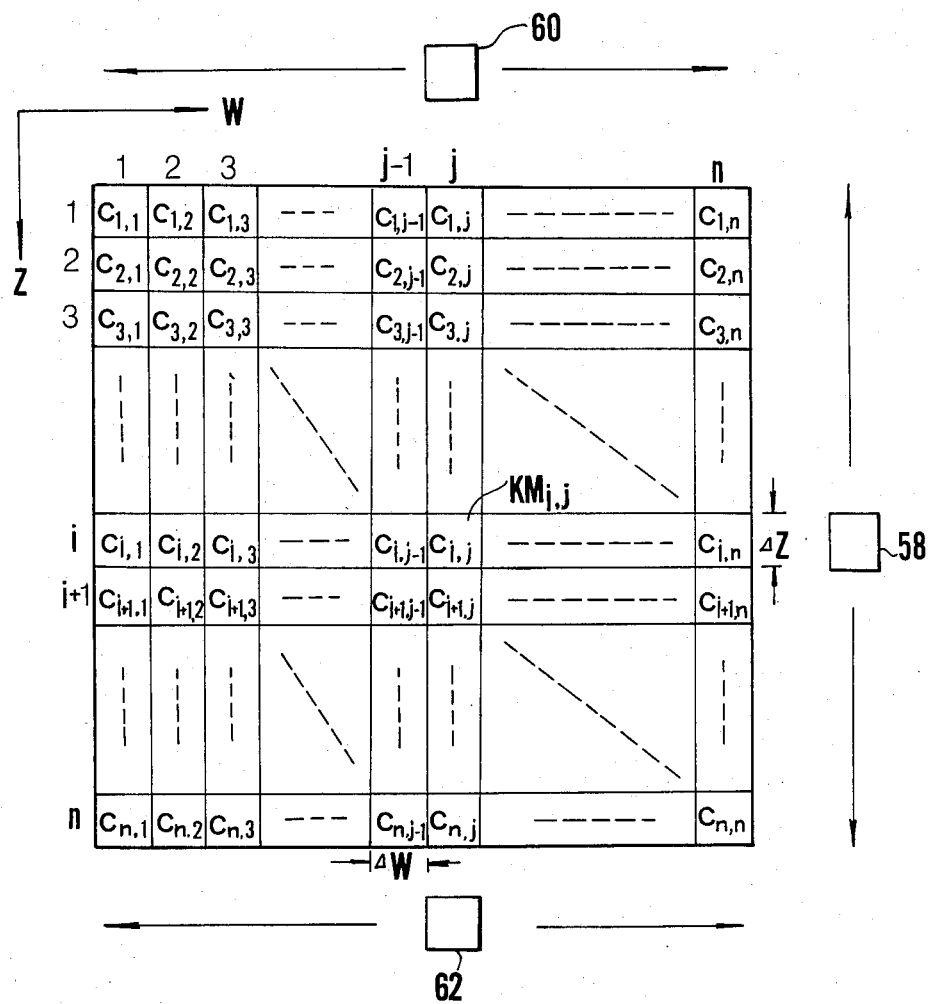
FIG. 11 is an explanatory view illustrating an imaginary matrix obtained as a result of partitioning a region of interest by scanning.
Figure 12:
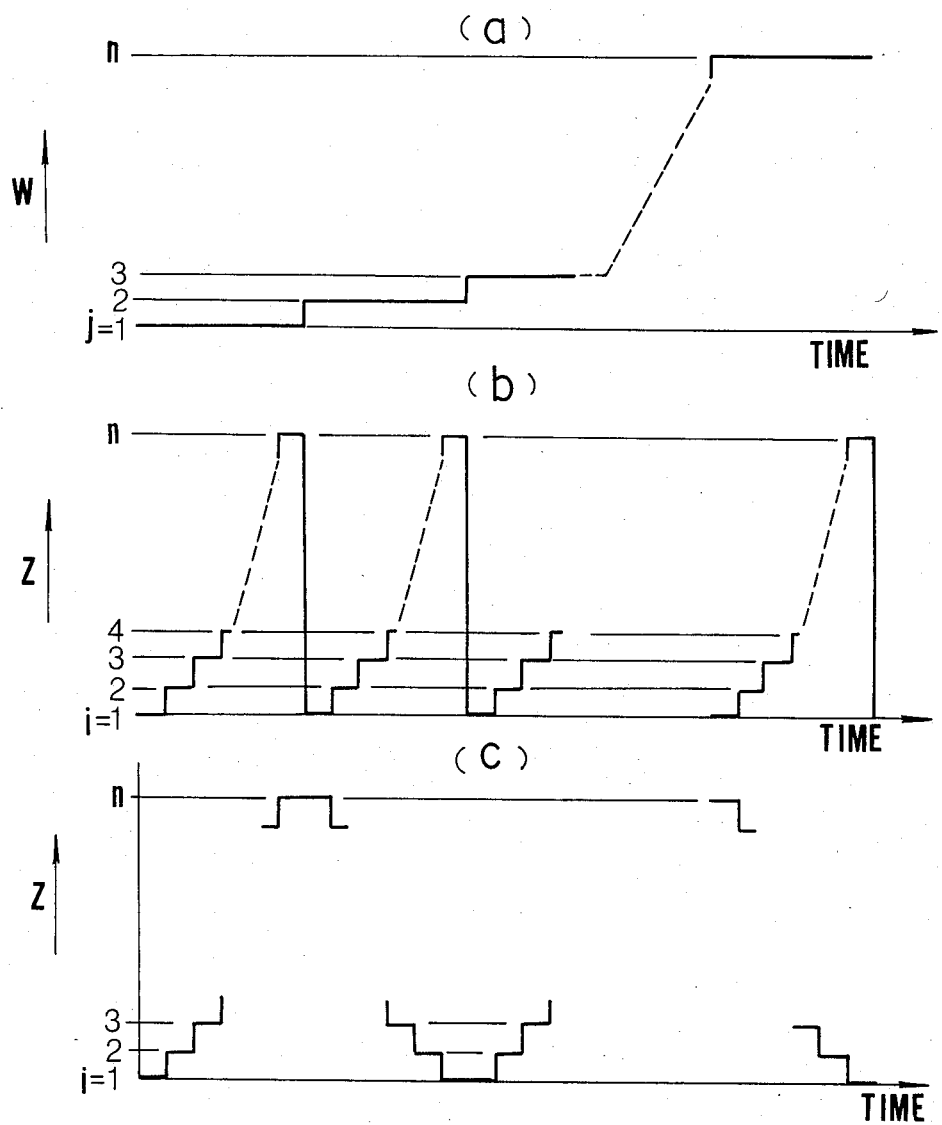
FIGS. 12(a) through (c) show diagrammatic representations illustrating ultrasonic probe scan timing.

To expand the foregoing in order to cover the entire object 14, the ultrasonic probes are made to scan in the manner shown in FIG. 10 to provide full coverage of the object. More specifically, as depicted in FIG. 10, the ultrasonic probes 60, 62 are moved intermittently and at the same time in a left-to-right direction w so that the position of the ray connecting these two probes is shifted by equal intervals from $j=1(=w)$ to $j=n(=w)$. At each position of the ray connecting the ultrasonic probes 60, 62, the other ultrasonic probe 58 is moved intermittently from top to bottom in FIG. 10 so that the position of its ray in the transmission direction is shifted by equal intervals from $i=1(=z)$ to $i=n(=z)$. In this way the entire scanned region is partitioned into an imaginery matrix KM of very small subdivisions each of which is bounded and delimited by the sonic rays, as shown in FIG. 11. It will suffice to find the propagation velocity $c_{i,j}$ of sound at each small subdivision $KM_{i,j}$ (, where it is assumed that $\Delta w = \Delta z$ holds) of the matrix by using the technique set forth in detail above. Possible scan timings for the probe pair 60, 62 and for probe 58 are as shown in FIGS. 12. In FIGS. 12(a) and 12(b), the probe pair 60, 62 [FIG. 12(a)] and the probe 58 [FIG. 12(b)] are made to scan from smaller to larger coordinate values. An alternative scanning schedule for the probe 58 is as shown in FIG. 12(c), in which the probe performs a reciprocative scanning operation. Specifically, the probe 58 is made to scan from smaller to larger coordinate values to vary z from 1 to n at w=i, and then is made to scan from larger to smaller coordinate values to vary z from n to 1 at the next point w=i+1.

Figure 13:
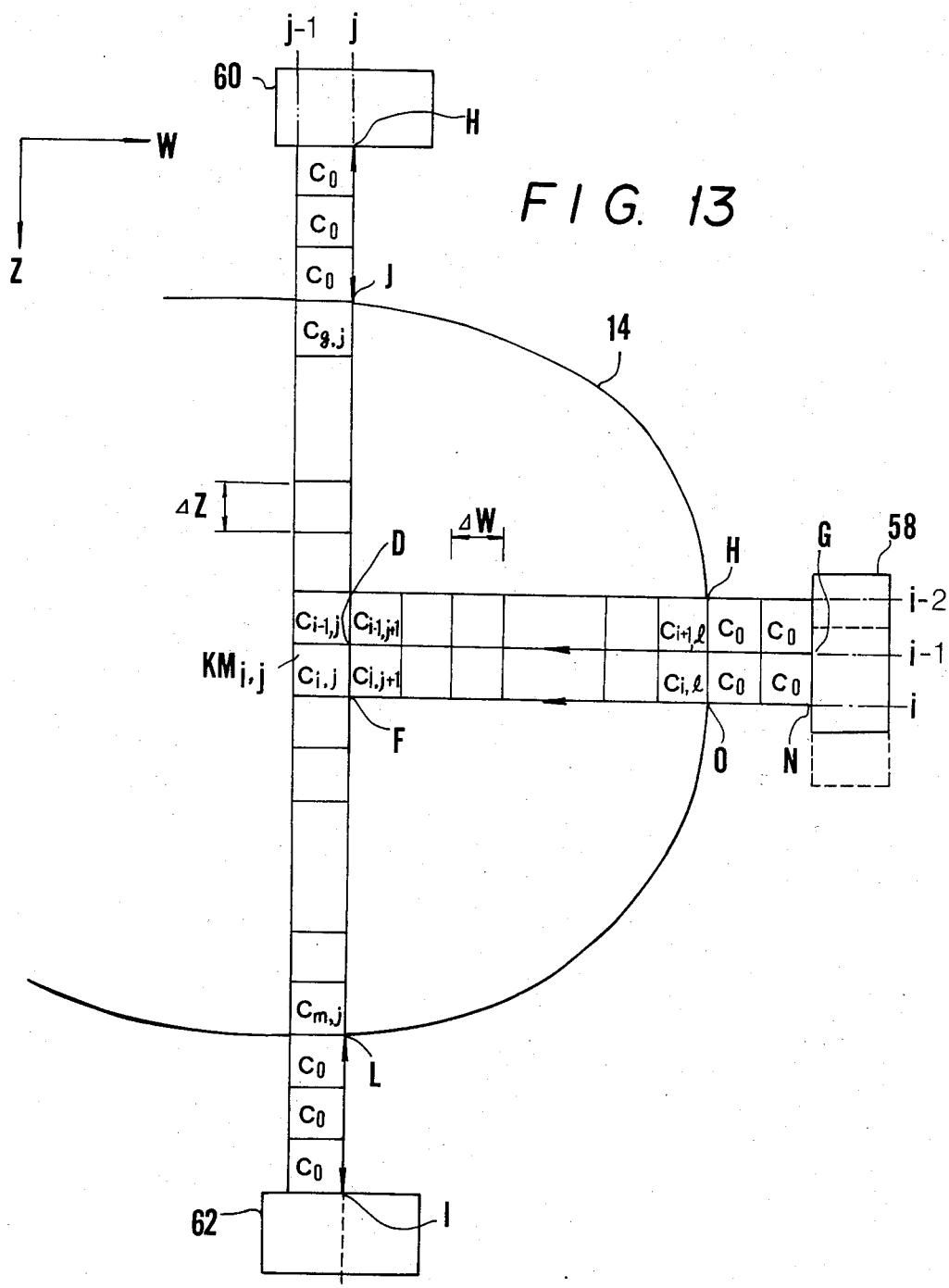
FIGS. 13 and 14 are detailed diagrammatic views useful in describing a sonic distribution measurement principle.
Figure 14:
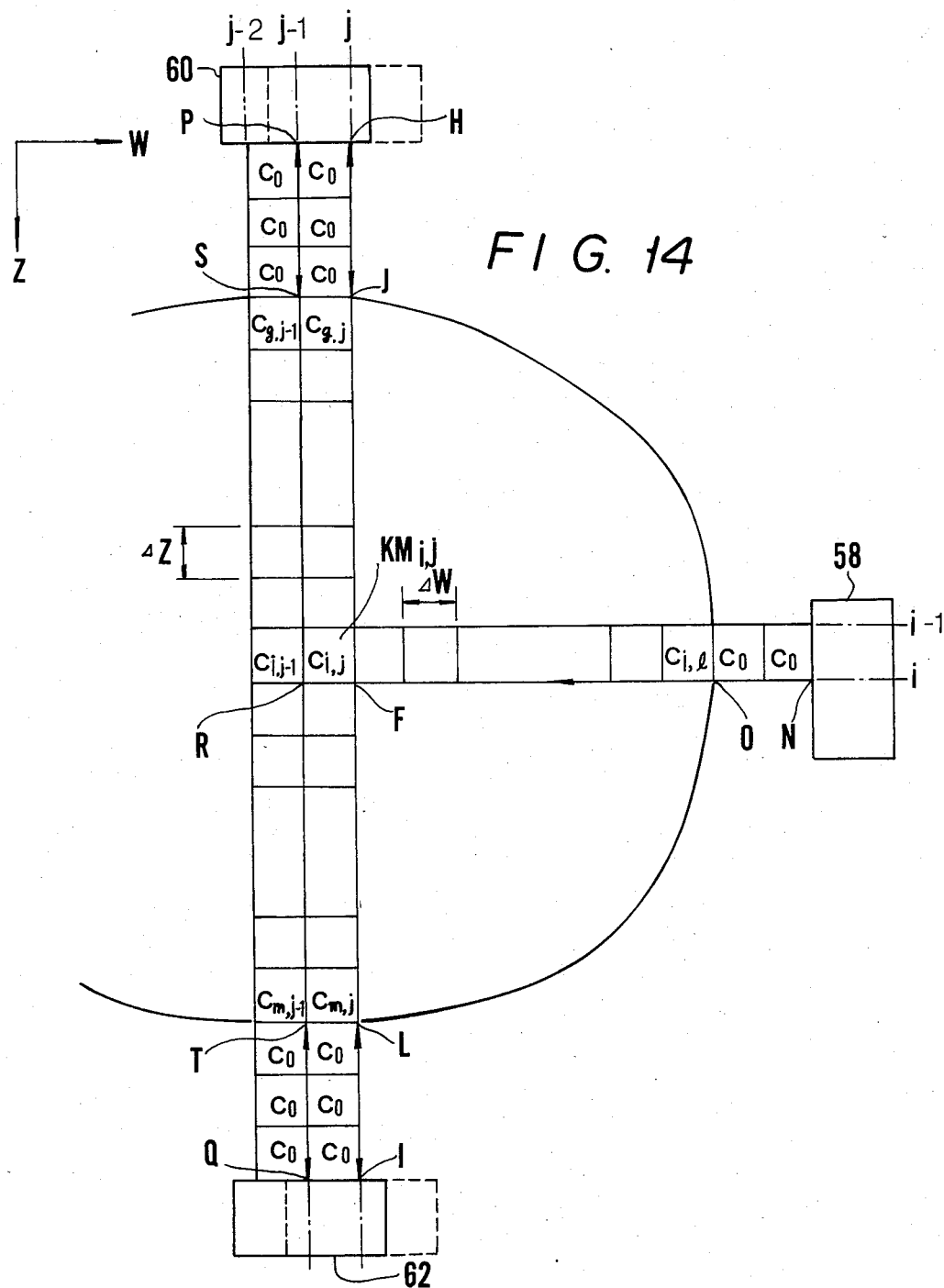

Reference will now be had to FIGS. 13 and 14 to describe in more concrete terms a method of measuring a distribution of propagation velocity of sound in an arrangement where a known medium is disposed between the object and each of the ultrasonic probes and the region under measurement is partitioned into the aforementioned imaginery matrix KM. FIG. 13 is useful in describing calculation of a propagation velocity $c_{i,j}^{(z)}$ of sound in the z direction in a matrix subdivision $KM_{i,j}$, and FIG. 14 is useful in describing calculation of a propagation velocity $c_{i,j}^{(w)}$ of sound in the w direction in the same matrix subdivision $KM_{i,j}$.

With reference first to FIG. 13, there is shown a portion of the matrix bounded by the rays $w=j-1, j$ and $z=i-2, i-1, i$. Portions inside the object 14 having the subscripts g through m ($1<g<m<n$) with regard to i and with the subscripts j through l ($1<j<1<n$) with regard to j are expressed by matrix subdivisions in which the propagation velocity of sound is $c_{i,j}$. Portions in the known medium 56 (i.e., outside the object 14) are expressed by matrix subdivisions where the propagation velocity of sound is $c_0$. Assume that the ultrasonic probes 60, 62 are at the points H, I, respectively, that the position of the ray connecting these two probes is $w=j$, that the ultrasonic probe 58 is at the point G, and that the position of the ray of probe 58 in the direction of transmission is at $z=i-1$. Under these conditions, let $T_{60}^{58}(i-1,j)$ represent the time required for an ultrasonic pulse from the ultrasonic probe 58 to reach the ultrasonic probes 60, 62 following scattering at the point D. The propagation velocity of sound in the zone between the points D and F may be expressed as follows by referring to Eq. (48) or (49):

$$c = 2\Delta z/[T_{60}^{58}(i,j) - T_{62}^{58}(i,j) - T_{60}^{58}(i-1,j) + T_{62}^{58}(i-1,j)] \quad (50)$$

or $$c = 2\Delta z/[T_{62}^{58}(i,j) - T_{60}^{58}(i,j) - T_{62}^{58}(i-1,j) + T_{60}^{58}(i-1,j)] \quad (51)$$

This value of c is the propagation velocity $c_{i,j}^{(z)}$ of sound in the z direction in the matrix subdivision $KM_{i,j}$.

FIG. 14 illustrates a portion of the matrix bounded by the rays $w=j-2, j-1, j$ and $z=i-1, i$. Assume that the ultrasonic probe 58 is at the point N, and that the ultrasonic probes 60, 62 are at points P, Q, respectively. Under these conditions, let R represent the scattering point, and let $t_{13}, t_{14}, t_{15}$ represent the periods of time required for an ultrasonic wave to propagate across NR, RP and RQ.

The periods of time required for an ultrasonic pulse from the ultrasonic probe 58 to reach the ultrasonic probes 60, 62 following scattering at the point R are expressed as follows:

$$T_{60}^{58}(i,j-1) = t_{13} + t_{14} \quad (52)$$

$$T_{62}^{58}(i,j-1) = t_{13} + t_{15} \quad (53)$$

and the period of time required for an ultrasonic pulse from the ultrasonic probe 60 to reach the ultrasonic probe 62 by passing through the object 14 is expressed by the following equation:

$$T_{62}^{60}(j-1) = t_{14} + t_{15} \quad (54)$$

The period of time $t_{13}$ may be found from Eqs. (52), (53), (54) as follows:

$$t_{13} = [T_{60}^{58}(i,j-1) + T_{62}^{58}(i,j-1) - T_{62}^{60}(j-1)]/2 \quad (55)$$

Leaving the ultrasonic probe 58 at the point N and placing the ultrasonic probes 60, 62 at the points H, I, respectively, we let $t'_{13}, t'_{14}, t'_{15}$ represent the periods of time required for an ultrasonic wave to propagate across NF, FH and FI, with F being the scattering point. We may then derive the following:

$$T_{60}^{58}(i,j) = t'_{13} + t'_{14} \quad (56)$$

$$T_{62}^{58}(i,j) = t'_{13} + t'_{15} \quad (57)$$

$$T_{62}^{60}(j) = t'_{14} + t'_{15} \quad (58)$$

Using these three equations, we find $t'_{12}$ as follows:

$$t'_{13} = [T_{60}^{58}(i,j) + T_{62}^{58}(i,j) - T_{62}^{60}(j)]/2 \quad (59)$$

Therefore, the velocity at which sound propagates across the scattering points R, F may be calculated from the following equation:

$$c = \Delta w/(t_{13} - t'_{13})$$
$$= 2\Delta z/\{[T_{60}^{58}(i,j-1) + T_{62}^{58}(i,j-1) - T_{62}^{60}(j-1)] - [T_{60}^{58}(i,j) + T_{62}^{58}(i,j) - T_{62}^{60}(j)]\} \quad (60)$$

This value of c is the propagation velocity $c_{i,j}^{(w)}$ of sound in the w direction in the matrix subdivision $KM_{i,j}$.

If the object 14 does not exhibit anisotropy with respect to the velocity of sound, the average of the values $c_{i,j}^{(z)}, c_{i,j}^{(w)}$ obtained from Eq. (50) or Eqs. (51) and (60) may be treated as the propagation velocity of sound in the matrix subdivision $KM_{i,j}$. Where anisotropy is present, however, as in muscle tissue, $c_{i,j}^{(z)}, c_{i,j}^{(w)}$ are treated as separate values.

An embodiment of an ultrasonic measurement apparatus according to the present invention will now be described in detail with reference to FIG. 15 for a case where mean propagation velocity of sound and distribution of propagation velocity of sound in a human breast are measured by a water-immersion method in which a human breast is the object under examination and degased water serving as the known medium is disposed between the object and each of the ultrasonic probes.

Figure 15A:
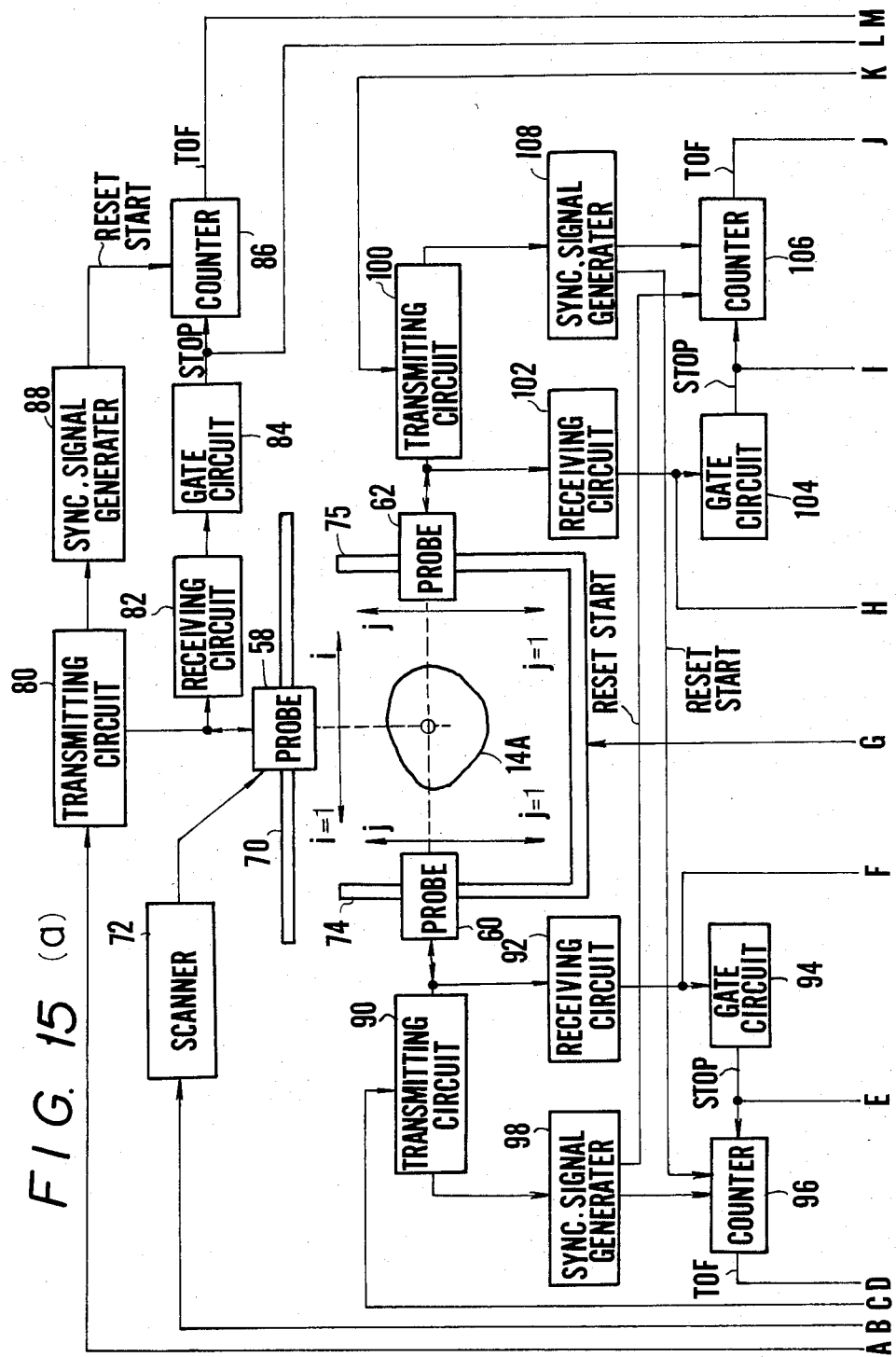
FIGS. 15(a) and (b) are block diagrams illustrating the arrangement of an ultrasonic measurement apparatus for practicing the method of the present invention.
Figure 15B:
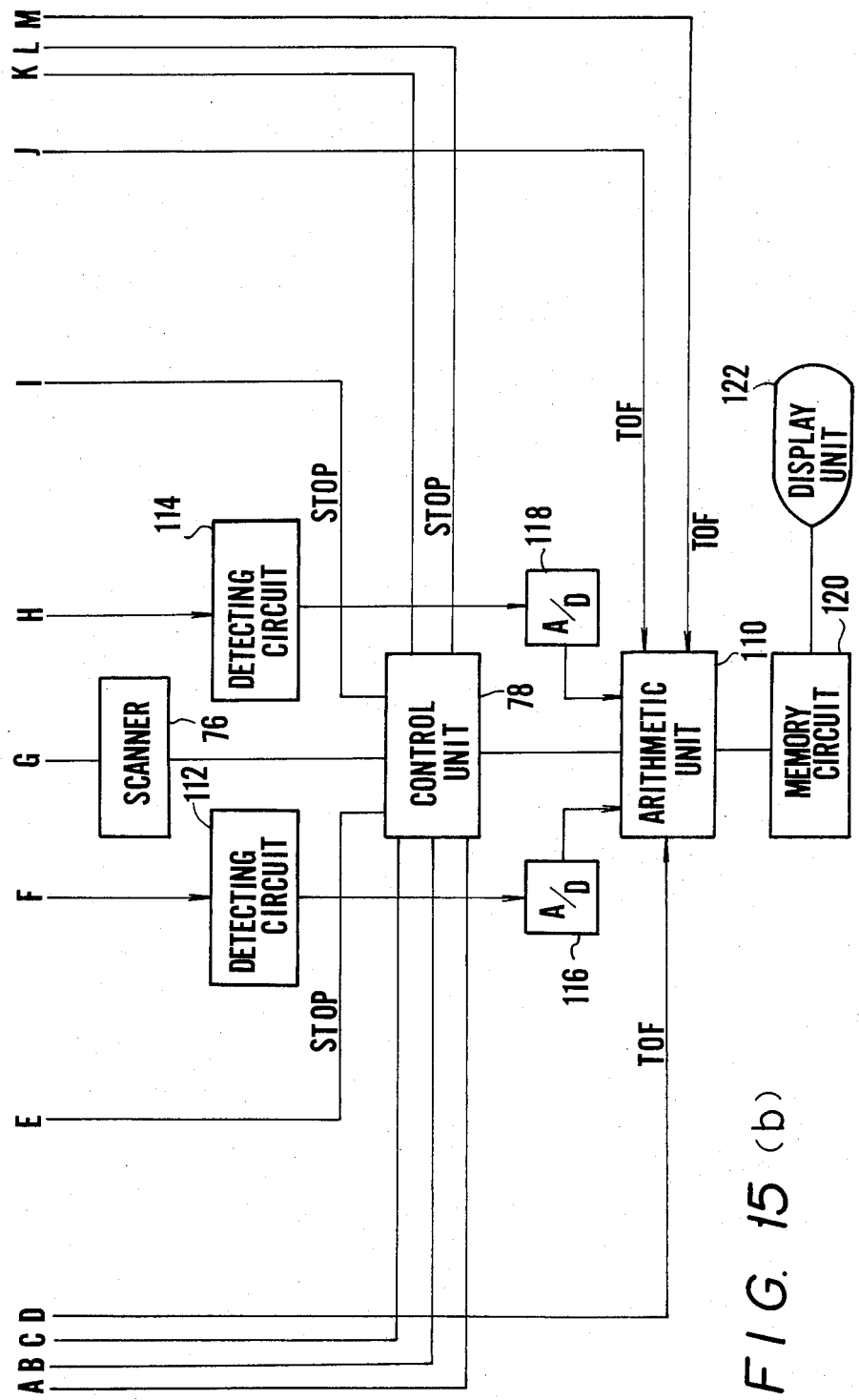
Figure 16:
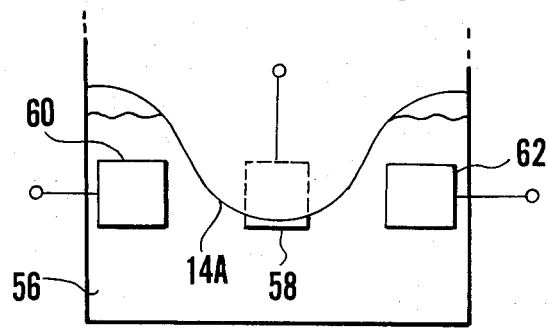
FIG. 16 is a diagrammatic longitudinal section illustrating an arrangement set up about a human breast serving as the object under examination in FIG. 15.

FIGS. 15(a) and (b) are block diagrams illustrating the overall construction of the ultrasonic measurement apparatus. The ultrasonic probes 60, 62 are set up in direct opposition across a object 14A, and the ultrasonic probe 58 is placed in a predetermined positional relationship with respect to the others probes at right angles to the straight line connecting the probes 60, 62. Each of the ultrasonic probes 58, 60, 62 is capable of both transmission and reception and is placed in the same horizontal plane in degased water 56 about the object 14A, as depicted in FIG. 16. The ultrasonic probe 58 is arranged to be freely slidable along a feed guide 70 extending transversely of FIG. 15(a) and is made to perform a linear scan from $z=1$ to $z=n$ in the z direction under drive supplied by a scanner 72. The ultrasonic probes 60, 62 are arranged to be freely slidable along respective feed guides 74, 75 extending vertically of FIG. 15(a) and perform a linear scan in unison from w=1 to w=n in the w direction (upwardly in FIG. 15(a)) under drive supplied by a scanner 76. The scanners 72, 76 perform a scanning operation through a sequence of the type shown in FIGS. 12(a), (b) under the control of a control circuit 78, described below.

Connected to the ultrasonic probes 58, 60, 62 are transmitting circuits 80, 90, 100 and receiving circuits 82, 92, 102, respectively. In response to transmission timing signals applied thereto individually by the control unit 78, the transmitting circuits 80, 90, 100 deliver single-pulse signals to the respective ultrasonic probes 58, 60, 62 which are activated thereby to emit an ultrasonic pulse. Upon receiving the ultrasonic pulses from the respective ultrasonic probes 58, 60, 62 connected thereto, the receiving circuits 82, 92, 102 amplify the received signals at a rapid rate and deliver them as output signals to respective noise-removal gate circuits 84, 94, 104. These apply the signals to respective propagation time counters 86, 96, 106 following noise removal. The outputs of the gate circuits 84, 94, 104 serve as stop signals (denoted as STOP in the drawings) which halt the counting operation of the respective counters 86, 96, 106. The stop signals are also applied to the control unit 78.

Connected to the output sides of the transmitting circuits 80, 90, 100 are synchronizing signal generating circuits (denoted as SYNC. SIGNAL GENERATOR in the drawing) 88, 98, 108, respectively. These are separately provided with the single-pulse signals that the transmitting circuits 80, 90, 100 deliver to the ultrasonic probes 58, 60, 62 and effect a predetermined time delay from receipt of these signals to produce reset/start signals timed to coincide with the instants at which the ultrasonic pulses are transmitted by the respective ultrasonic probes 58, 60, 62. The reset/start signals are applied to the respective counters 86, 96, 106 to start them counting at the aforementioned timing. The outputs of the synchronizing signal generating circuits 98, 108 are applied as reset/start signals to the respective counters 106, 96 as well. Each of the counters 86, 96, 106 also receives a high-rate clock input for count-up purposes. In response to the reset/start signal, each of the counters 86, 96, 106 has its status cleared and then immediately starts counting until the stop signal arrives. The count recorded by each of the counters 86, 96, 106 is delivered as propagation time data to an arithmetic unit 110. Note that in order to identify biological tissue having a size of 2 mm at a 1% difference in propagation velocity of sound, the TOF measurement precision required is at least $$0.667[\mu_s/mm] \times 2[mm] \times 1[\%] = 13n_s$$

assuming that in vivo mean propagation velocity of sound is 1,500m/B (1.5 mm/$\mu_s$→0.667 $\mu_s$/mm). For a value of 10$n_s$, the counters should be capable of counting at a rate of 100 MHz. Analog-to-digital (A/D) converters 116, 118 are connected to the output sides of the receiving circuits 92, 102 via detector circuits 112, 114, respectively, to detect the received signals and convert them into DC components. The reception signal data obtained in the form of digital values by the operation of the A/D converters 116, 118 are delivered to the arithmetic unit 110. The A/D converters 116, 118 are for the purpose of specifying the points in time at which the received signals reach their peak values so that the peaks of these signals can be detected by the arithmetic unit 110.

On the basis of the input data from the counters 86, 96, 106 and A/D converters 116, 118, and in accordance with the prescribed methodology described earlier, the arithmetic unit 110 calculates the mean propagation velocity of sound along each of the aforementioned ray intervals inside the object 14A, or the distribution of propagation velocity of sound inside the object. The results of calculation are stored in a memory circuit 120 connected to the output side of the arithmetic unit 110 and are displayed as necessary on a display unit 122 in the form of numerical values when the information of interest is the mean propagation velocity of sound along each ray interval, and in the form of a tomograph obtained by luminance modulation of propagation velocity of sound when the information of interest is the distribution of propagation velocity of sound.

Figure 17:
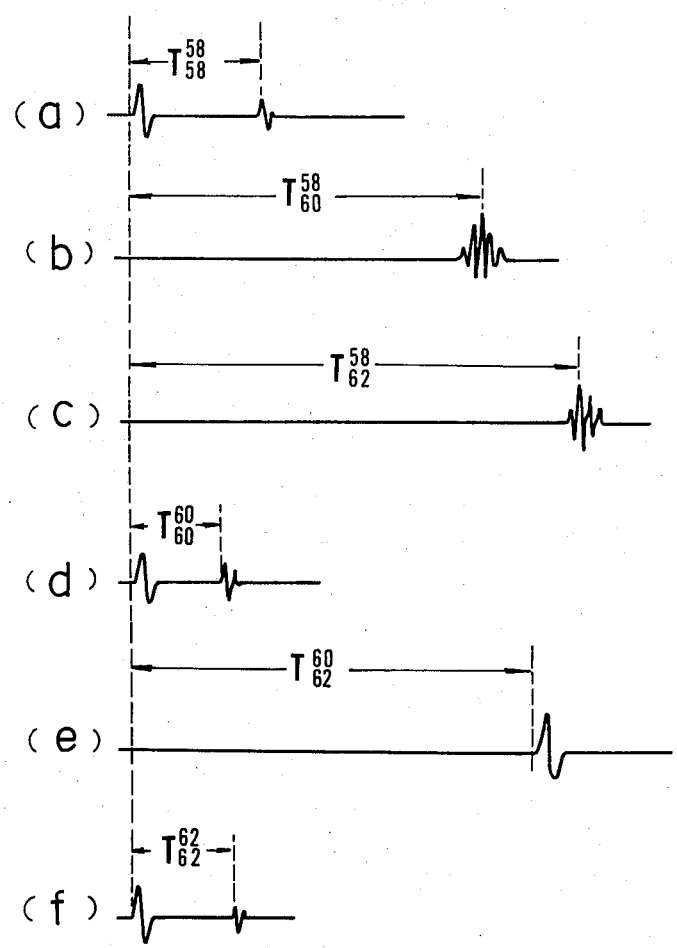
FIGS. 17(a) through (f) show diagrammatic representations illustrating waveforms transmitted and received by each of the ultrasonic probes.

The transmitted and received waveforms which prevail when an ultrasonic pulse is transmitted by the ultrasonic probe 58 and received by the ultrasonic probes 60, 62 are illustrated in FIGS. 17(a) through (c). Specifically, (A) shows the transmitted waveform while (b) and (c) depict the waveforms received by the probes 60, 62, respectively. [It should be noted that the later occurring waveforms in FIGS. 17(a), (d) and (f) indicate reflected waves from the surface of the object.) Likewise, the transmitted and received waveforms which prevail when an ultrasonic pulse is transmitted by the ultrasonic probe 60 and received by the ultrasonic probe 62 are illustrated in FIGS. 17(d) and (e), respectively. FIG. 17(f) illustrates the waveform of the ultrasonic pulse transmitted by the ultrasonic probe 62, as well as the form of the wave received by the same probe 62 following reflection at the surface of the object.

CONCRETE OPERATION OF THE INVENTION

Figure 18:
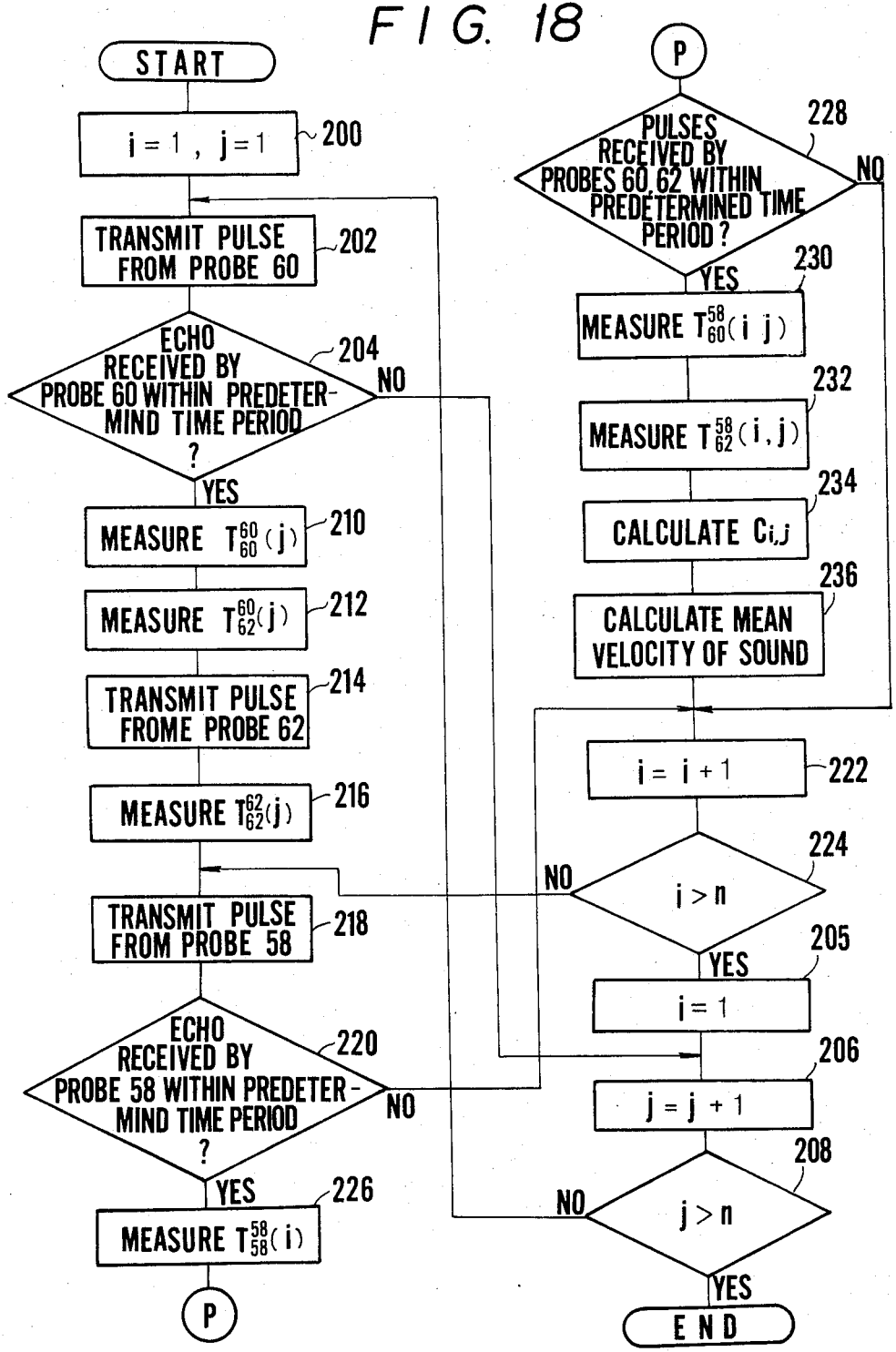
FIG. 18 is a flowchart illustrating the overall operation of the ultrasonic measurement apparatus shown in FIGS. 15(a) and (b)

The overall operation of the ultrasonic measurement apparatus embodied hereinabove will now be described with reference to the flowchart of FIG. 18.

The control sequence indicated by the flowchart is stored in an interval memory (not shown) of the control unit 78 and is executed by a microprocessor or the like, not shown. As for the directions in which the ultrasonic probes are made to scan in the flowchart, the probes 60, 62 perform scanning in accordance with the method of FIG. 12(a), and the probe 58 in accordance with the method of FIG. 12(b).

In an initial setting step 200 of the flowchart, the ultrasonic probe 58 is moved to position i=1 and the ultrasonic probe pair 60, 62 is moved to position j=1 by the scanners 72, 76, respectively. This is followed by executing step 202 of the flowchart, in which the transmitting circuit 90 is placed in operation to transmit an ultrasonic pulse toward the object 14A. The counter 96 begins counting at this time. In accordance with the timing of the stop signal input from the gate circuit 94, the control unit 78 determines at a step 204 whether the receiving circuit 92 receives an echo before lapse of a predetermined period of time from transmission of the ultrasonic pulse. (Note that the probe 60 will receive an echo owing to reflection at the surface of the object 14A 80 microseconds after transmission assuming that the velocity of sound in water is 1500 m/s and the probe 60 is at a distance of 6 cm from the surface of the object 14A.) If no echo is received within the predetermined time period, the control unit 78 renders a decision to the effect that the region of the object 14A has not yet been reached and advances the program to a step 206 to move the scanning position to j=2 by performing the operations j=j+1 without executing processing for calculation of propagation velocity of sound. The control unit 78 then determines at a step 208 whether j>n holds. If the decision is negative, then the system moves back to the step 202.

When the decision at the step 204 is that a reflected wave has been received within the predetermined time period, the counter 96 is caused to stop counting and the count recorded thereby is read in by the arithmetic unit 110 at a step 210 as data representative of round-trip propagation time $T_{60}^{60}(j)$ to the surface of the object 14A and back. Further, the counter 106 associated with the ultrasonic probe 62 starts counting in response to the reset/start signal delivered by the synchronizing signal generating circuit 98 at the instant of the transmission from the ultrasonic probe 60. When the ultrasonic pulse from the probe 60 is received by the probe 62 by passing through the object 14A, the gate circuit 104 produces the stop signal in response to which the counter 106 stops counting. The control unit 78 is also responsive to the stop signal to cause the arithmetic unit 110 to read in, at a step 212, the status of the counter 106 as data $T_{62}^{60}(j)$.

In a manner similar to the foregoing, the ultrasonic probe 62 transmits an ultrasonic pulse at a step 214 and $T_{62}^{62}(j)$ is measured at a step 216.

Next, the ultrasonic probe 58 transmits an ultrasonic pulse toward the object at a step 218. This is followed by a step 220, at which it is determined whether a reflected wave has been received from the surface of the object 14A. If the decision is negative, then this indicates that measurement of propagation velocity of sound is both unnecessary and impossible, as set forth above. The scanning position is therefore made $i=i+1=2$ at a step 222, and it is decided at a step 224 whether the inequality i>n holds. If it does not, processing returns to the step 218 and the loop constituted by steps 218, 220, 222, 224 218 is repeated in the order mentioned until the ultrasonic probe 58 enters the region of the object 14A. If l>n does hold at step 224, then the next step executed is 206 for $j=j+1$.

When the decision rendered at the step 220 is that a reflected wave has been received, $T_{58}^{58}(i)$ is measured at a step 226. This is followed by a step 228, at which it is determined whether the ultrasonic pulse transmitted by the ultrasonic probe 58 has been received by the ultrasonic probes 60, 62. If even one of the probes 60, 62 has failed to receive the pulse, measurement according to the principle of the present invention is impossible and the next step executed is a step 222. A state in which measurement is impossible even though the rays of the ultrasonic probes 58, 60, 62 are within the object 14A occurs when the intersection of the rays from the three probes lies outside the object. When both of the probes 60, 62 receive the pulse, the instants at which the levels of the reception signals peak are detected based on the outputs data from the A/D converters 116, 118, a time difference is found relative to a transmission timing signal delivered by the control unit 78 (see $T_0$ in FIG. 7), and $T_{60}^{58}(i,j)$, $T_{62}^{58}(i,j)$ are measured at steps 230, 232.

Figure 19:
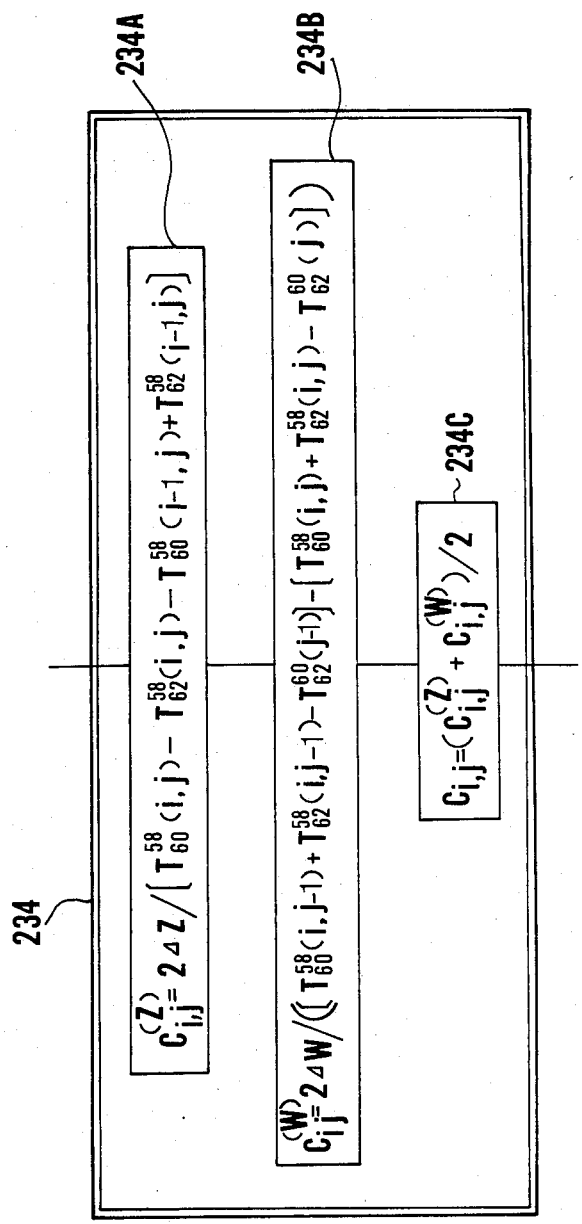
FIG. 19 is a flowchart illustrating an algorithm for calculation of a distribution of propagation velocity of sound.

When the necessary data $T_{62}^{60}(j)$, $T_{60}^{58}(i,j)$, $T_{62}^{58}(i,j)$ obtained by the foregoing measurements are ready and it becomes possible to calculate a distribution of propagation velocity of sound, a step 234 is executed to calculate $c_{i,j}^{(z)}$ and $c_{i,j}^{(w)}$ in accordance with Eqs. (50), (60) above, with these values being averaged to obtain the propagation velocity $c_{i,j}$ of sound i.e., $c_{i,j}=[c_{i,j}^{(z)}+c_{i,j}^{(w)}]/2$. Averaging is allowed because the object 14A is not anisotropic. The details of the calculation process are given by the algorithm of steps 234A through 234C of the flowchart shown in FIG. 19.

Likewise, when the items of data $T_{60}^{60}(j)$, $T_{62}^{60}(j)$, $T_{62}^{62}(j)$, $T_{58}^{58}(i)$, $T_{60}^{58}(i,j)$, $T_{62}^{58}(i,j)$ are ready so that calculation of mean propagation velocity of sound is possible, a step 236 is executed to obtain the mean propagation velocities $c_8(i,j)$, $c_9(i,j)$, $c_{11}(i,j)$ of sound along the three ray intervals in accordance with Eqs. (23), (27), (29) given earlier. The value of the propagation velocity $c_{i,j}$ of sound and the values of mean propagation velocity of sound are stored in the memory circuit 120.

The foregoing calculations are performed in a case where calculation of the propagation velocity of sound and mean propagation velocities of sound is possible. Where impossible, none of the calculations at steps 234, 236 are made and the value of i is subsequently incremented at the step 222 to shift the ultrasonic probe 58 to the next scanning position. Then, at the stop 224, it is determined whether i>n holds. If the answer is NO, processing returns to the step 218, an ultrasonic wave is again transmitted by the probe 58, and the steps 218, 220, 226, 228, 230, 232, 234, 236, 222, 224, 218 are repeated in the order mentioned. When the decision rendered at the step 224 is that i>n holds, the program is advanced to a step 205 for the operation i=1 to return the ultrasonic probe 58 to its original position, and j is incremented at the step 206 to shift the probe pair 60, 62 to the next scanning position. It is then determined at the step 208 whether j>n holds. If the answer is negative, the program returns to the step 202 to repeat processing from the step for transmission of the ultrasonic wave by the probe 60. When the inequality j>n is established, this indicates the end of scanning for the entirety of the region of interest. Scanning is therefore halted. When the calculations for the propagation velocity $c_{i,j}$ of sound and for the mean propagation velocities of sound of the object 14A are thus completed, the velocity $c_{i,j}$ is subjected to luminance modulation for display as the tomograph of the distribution of propagation velocity of sound. Meanwhile, the mean propagation velocities of sound are displayed in the form of numerical data.

Figure 8:
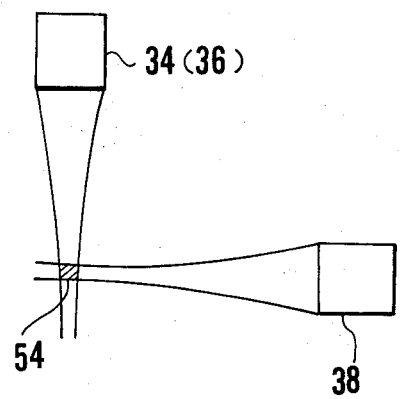

In FIG. 8, note that a region 54 where the rays of the ultrasonic probes 38, 34(36) intersect coincides with the focal regions of these ultrasonic probes. In order to move this region over the entirety of the object 14A, a ring-shaped probe capable of so-called "dynamic focusing" can be used.

Figure 20:
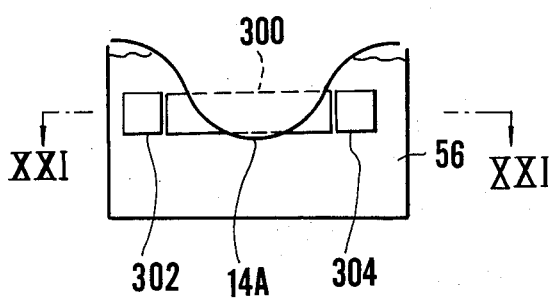
FIG. 20 is a diagrammatic longitudinal section illustrating an arrangement set up about a human breast when using linear array-type probes.
Figure 21:
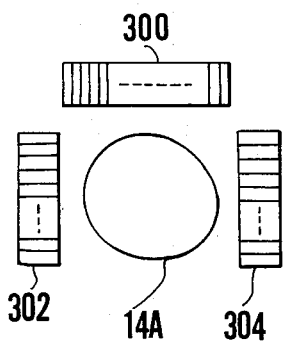
FIG. 21 is a horizontal section taken along line XXI—XXI of FIG. 20.
Figure 22:
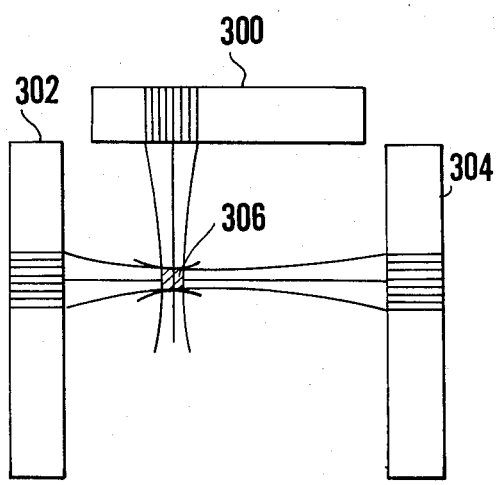
FIGS. 22 and 23 are views useful in describing operation and illustrate dynamic focusing of linear array-type probes.
Figure 23:
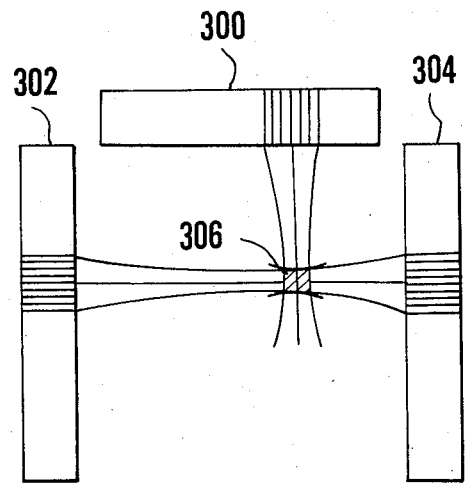

In the embodiment described above, three discrete ultrasonic probes are used and are mechanically transported for sliding motion to perform linear scanning. In another especially preferred embodiment shown in FIGS. 20 and 21, however, use can be made of three linear array-type ultrasonic probes 300, 302, 304 arranged in a U-shaped configuration about the object 14A. In this set-up, the above-described mechanical linear scanning is replaced by linear electronic scanning to raise scanning speed and to competely dispense with mechanical, moving parts. This arrangement therefore has the advantage of much higher scanning accuracy. When the linear array-type ultrasonic probes 300, 302, 304 are used, the region 306 of intersection at the focal regions can be moved over the entirety of the region of interest by a dynamic focusing technique as illustrated in FIGS. 22 and 23.

Figure 24:
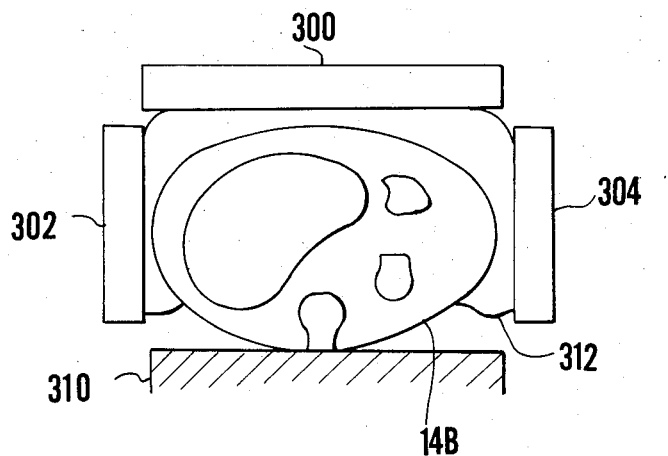
FIG. 24 is a diagrammatic explanatory view illustrating an embodiment in which the human abdomen is the object under examination.

Let us now refer to FIG. 24 to describe an embodiment in which the object under examination is the human abdomen. Since the abdomen of a human being does not readily lend itself to application of the water-immersion method used in examining the human breast, the body is kept at rest on a table 310 and a water bag 312 for purposes of acoustic coupling is provided between the surface of the abdomen 14B and the ultrasonic probes 300, 302, 304, which are of the above-described linear-array configuration. The probes are held fixed in a predetermined positional relationship by suitable fixing means, not shown. In other aspects the set-up and operation are as described above in connection with the examination of the breast as depicted in FIGS. 15(a) and (b), with the region of interest being scanned and the mean propagation velocities of sound and distribution of propagation velocity of sound being measured.

Figure 25:
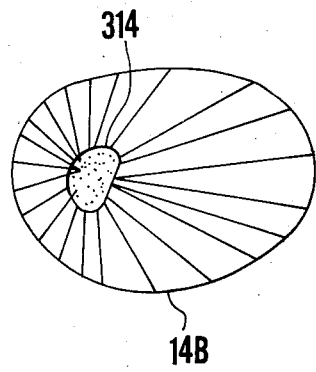
FIGS. 25 and 26 are views illustrating tomographs obtained by conventional ultrasonic computed tomography where gas and bone are present, respectively.
Figure 26:
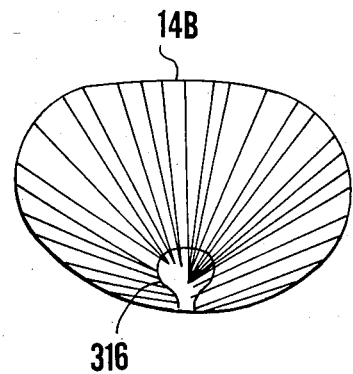

When the object under examination is the human abdomen, a problem is encountered in the prior-art method of ultrasonic computed tomography. Specifically, as touched upon in the above-cited "Image Processing for Medical Engineering", p.p. 296-297 (edited by Morio Onoe), an ultrasonic beam will not pass through bone or gas. Consequently, with the conventional method of ultrasonic CT using a transmission method, the projection data are incomplete and reconstruction into a tomograph is not possible. This may be understood more fully from FIG. 25, in which a zone 314 of accumulated gas is shown to be present in the abdomen 14B. The reconstructed tomograph in such case develops so-called "streaking" centered about the zone 314, so that a utilizable tomograph cannot be obtained. The tomograph suffers from the same phenomenon owing to the presence of a spinal column 316, as depicted in FIG. 26.

By contrast, the presence of bone or gas has minimal influence where the present invention is applied. This will now be described with reference to FIGS. 27 and 28.

Figure 27:
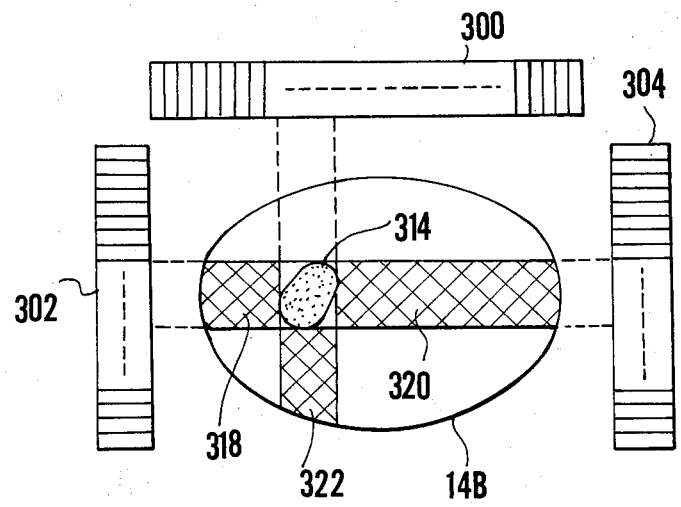
FIGS. 27 and 28 are diagrammatic explanatory views illustrating range of application in a object in accordance with the present invention.

When the gaseous zone or region 314 is present as shown in FIG. 27, transmission data cannot be obtained from the probes 302, 304 at the location of the gaseous region 314 and therefore the distribution of propagation velocity of sound and mean propagation velocities of sound for the regions 318, 320 cannot be measured. Further, the ultrasonic pulse from the probe 300 will not travel beyond the gaseous region 314 so that the distribution of propagation velocity of sound for the region 322 also cannot be measured. However, quite unlike conventional ultrasonic CT, those areas outside of the cross-hatched regions 318, 320, 322 can have their distribution of propagation velocity of sound and mean propagation velocity of sound measured by applying the principle of the present invention. A comparison of the reproduced image of FIG. 27 according to the present invention with the image of FIG. 25 afforded by the conventional method clearly shows that the present invention minimizes the influence of gas.

Figure 28:
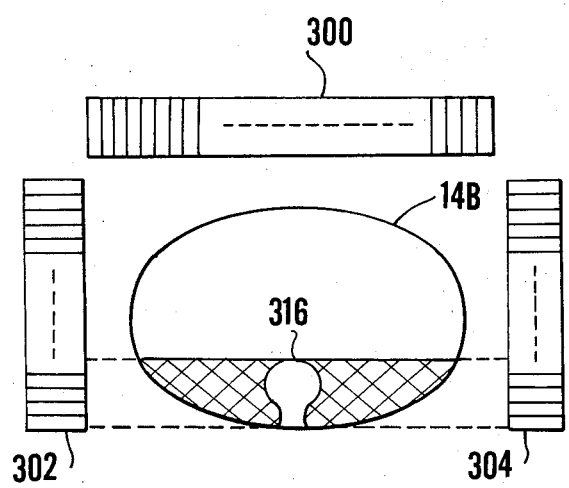

It should also be readily appreciated that the effect of the spinal column 316 is similarly minimized, as shown in FIG. 28.

Figure 29:
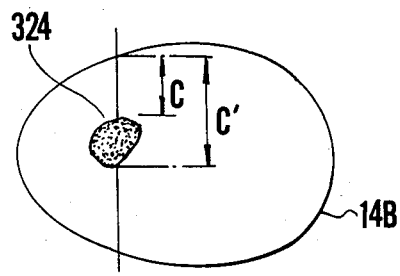
FIG. 29 is a diagrammatic explanatory view illustrating a method of obtaining mean propagation velocity of sound for an echo-free region.

Another advantageous feature of the invention will be understood from FIG. 29, in which the object 14B is shown to possess an echo-free region 324. This poses no problem as mean propagation velocity of sound internally of the region 324 can still be measured by finding the difference between a propagation velocity (value c) of sound up to the anterior of the region 324 and a propagation velocity (value c') of sound up to the posterior of the region 324 (i.e., by evaluating c'-c).

Figure 30:
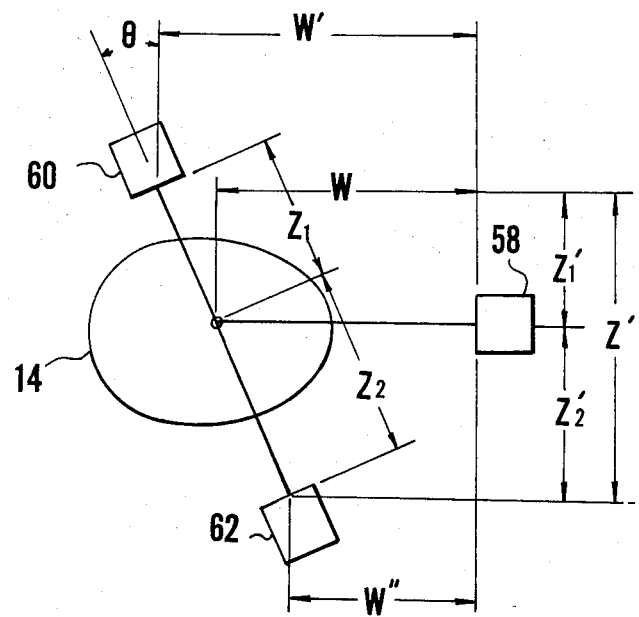
FIG. 30 is a diagrammatic explanatory view illustrating a principle of measurement in a case where ultrasonic probes are arranged in an angular positional relation.

In the embodiments described above, the pair of ultrasonic probes opposing each other across the object and the other single ultrasonic probe are arranged in an orthogonal relation. However, the present invention is not limited to such a configuration, for the ultrasonic probes 58, 60, 62 can also be disposed about the object 14 at predetermined angles and it will still be possible to measure mean propagation velocity of sound and distribution of propagation velocity of sound through entirely the same principles. For the case shown in FIG. 30, all that need be done is to substitute $z'_1/\cos\theta$, $z'_2/\cos\theta$ and $w'-z_1\tan\theta(=w''+z_2\tan\theta)$ for $z_1$, $z_2$ and w, respectivelyl, in Eqs. (23), (27) and (29). Furthermore, since ultrasonic pulses are transmitted and received in three directions with respect to the object in each of the foregoing embodiments, it is permissible to adopt an arrangement in which ordinary B-mode images are obtained for each of the three directions and combined.

CONCRETE EFFECT OF THE INVENTION

Thus, in accordance with the present invention, combining pulse-echo and transmission methods makes it possible to measure propagation velocity of sound internally of an object in a highly accurate manner without making special assumptions. In particular, distribution of propagation velocity of sound can be measured rapidly without the need for projection data 180° around the object, as is required with conventional ultrasonic computed tomography, and therefore it is unnecessary to use a special algorithm for image reconstruction, such as is typified by a filtered back projection. The invention is especially advantageous in that range of application, which was essentially limited to the human breast with conventional ultrasonic computed tomography, can be broadened to include such portions of the human body as the abdomen. And since in vivo propagation velocity of sound unobtainable with B-mode imaging can now be measured, highly diversified medical diagnosis is possible.

As many apparently widely different embodiments of the present invention can be made without departing from the spirit and scope thereof, it is to be understood that the invention is not limited to the specific embodiments thereof except as defined in the appended claims.

What is claimed is:

1. An ultrasonic measurement method in which first and second ultrasonic transducers constituting a set are arranged to directly oppose each other across an object interposed therebetween, a third ultrasonic transducer is provided at a predetermined position and directed toward the object, the first, second and third ultrasonic transducers being so arranged that a ray along a transmission direction of the third ultrasonic transducer intersects, internally of the object, a ray connecting the first and second ultrasonic transducers, said method comprising steps of:
   (a) transmitting an ultrasonic wave into the object from the first ultrasonic transducer;
   (b) measuring a first period of time required for the ultrasonic wave from the first ultrasonic transducer to be received by the second ultrasonic transducer by passing through the object;

(c) transmitting an ultrasonic wave into the object from the third ultrasonic transducer, said ultrasonic wave being scattered at a portion where the rays intersect;

(d) measuring second and third periods of time respectively required for the ultrasonic wave from the third ultrasonic transducer to be received by said first and second ultrasonic transducers following scattering of the ultrasonic wave; and (e) measuring mean propagation velocity of sound, on the basis of the first, second and third periods of time, along three ray intervals which are located inside the object and which connect the portion at which the rays intersect and each of the three ultrasonic transducers.

2. The ultrasonic measurement method according to claim 1, wherein the portion at which the rays intersect is made a focal region of the first, second and third ultrasonic transducers.

3. The ultrasonic measurement method according to claim 1, in which a medium of a known sonic velocity is disposed between the object and each of the first, second and third ultrasonic transducers, and comprising steps of:

(a') transmitting an ultrasonic wave toward the object from each of the first, second and third ultrasonic transducers;

(b') measuring fourth, fifth and sixth periods of time required for the ultrasonic waves from the first, second and third ultrasonic transducers to be received thereby, respectively, following reflection at object surface points nearest to the ultrasonic transducers; and (c') measuring mean propagation velocity of sound, on the basis of data inclusive of the fourth, fifth and sixth periods of time, along the three ray intervals which are located inside the object and which connect the portion at which the rays intersect and each of the three ultrasonic transducers.

4. An ultrasonic measurement method in which first and second ultrasonic transducers constituting a set are arranged to directly oppose each other across an object interposed therebetween, a third ultrasonic transducer is provided at a predetermined position and directed toward the object, the first, second and third ultrasonic transducers being so arranged that a ray along a transmission direction of the third ultrasonic transducer intersects, internally of the object, a ray connecting the first and second ultrasonic transducers, said method comprising steps of:

(a) succesively moving the intersection of the rays along a predetermined path of travel in a predetermined plane internally of the object to scan the intersection in said plane while a position of the ray connecting the first and second ultrasonic transducers and a position of the ray along the transmission direction of the third ultrasonic transducer are changed;

(b) performing the following steps at each point scanned:

(b₁) transmitting an ultrasonic wave into the object from the first ultrasonic transducer;

(b₂) measuring a first period of time required for the ultrasonic wave from the first ultrasonic transducer to be received by the second ultrasonic transducer by passing through the object;

(b₃) transmitting an ultrasonic wave into the object from the third ultrasonic transducer, said ultrasonic wave being scattered at the intersection of the rays; and (b₄) measuring second and third periods of time respectively required for the ultrasonic wave from the third ultrasonic transducer to be received by said first and second ultrasonic transducers following scattering of the ultrasonic wave;

(c) finding propagation velocity of sound between mutually adjacent intersections of the rays at each point scanned in accordance with a predetermined sequence and based on the first, second and third periods of time concerning said mutually adjacent intersections; and (d) successively calculating a distribution of propagation velocity of sound in said plane interiorly of the object based on the propagation velocities found in said step (c).

5. The ultrasonic measurement method according to claim 4, wherein the intersection of the rays is made a focal region of the first, second and third ultrasonic transducers.

6. An ultrasonic measurement apparatus comprising:

first and second ultrasonic transducers constituting a set and arranged to directly oppose each other across an object interposed therebetween, said first ultrasonic transducer being adapted to transmit an ultrasonic wave into the object;

a third ultrasonic transducer provided at a predetermined position and directed toward the object for transmitting an ultrasonic wave into the object, said first, second and third ultrasonic transducers being so arranged that a ray along a transmission direction of said third ultrasonic transducer intersects, internally of the object, a ray connecting the first and second ultrasonic transducers, the ultrasonic wave transmitted by said third ultrasonic transducer being scattered at a portion where the rays intersect;

time measuring means for measuring a first period of time required for an ultrasonic wave transmitted by said first ultrasonic transducer to be received by said second ultrasonic transducer by passing through the object, as well as second and third periods of time respectively required for an ultrasonic wave transmitted by said third ultrasonic transducer to be received by said first and second ultrasonic transducers following scattering of the ultrasonic wave; and propagation velocity measuring means for measuring mean propagation velocity of sound, on the basis of the first, second and third periods of time measured by said time measuring means, along three ray intervals which are located inside the object and which connect the portion at which the rays intersect and each of said ultrasonic transducers.

7. The ultrasonic measurement apparatus according to claim 6, wherein the portion at which the rays intersect is made a focal region of said first, second and third ultrasonic transducers.

8. The ultrasonic measurement apparatus according to claim 6, in which a medium of a known sonic velocity is disposed between the object and each of said, first, second and third ultrasonic transducers, and said second ultrasonic transducer is adapted to transmit an ultrasonic wave toward the object, wherein said time measuring means includes means for measuring fourth, fifth and sixth periods of time required for the ultrasonic waves from said first, second and third ultrasonic transducers to be received thereby, respectively, following reflection at object surface points nearest to said ultrasonic transducers, and said propagation velocity measuring means includes means for measuring mean propagation velocity of sound, on the basis of data inclusive of the fourth, fifth and sixth periods of time, along the three ray intervals which are located inside the object and which connect the portion at which the rays intersect and each of said ultrasonic transducers.

9. An ultrasonic measurement apparatus comprising:
first and second ultrasonic transducers constituting a set and arranged to directly oppose each other across an object interposed therebetween, said first ultrasonic transducer being adapted to transmit an ultrasonic wave into the object;
a third ultrasonic transducer provided at a predetermined position and directed toward the object for transmitting an ultrasonic wave into the object, said first, second and third ultrasonic transducers being so arranged that a ray along a transmission direction of said third ultrasonic transducer intersects, internally of the object, a ray connecting the first and second ultrasonic transducers, the ultrasonic wave transmitted by said third ultrasonic transducer being scattered at the intersection of the rays;
scanning means for successively moving the intersection of the rays along a predetermined path of travel in a predetermined plane internally of the object to scan the intersection in said plane while a position of the ray connecting said first and second ultrasonic transducers and a position of the ray along the transmission direction of said third ultrasonic transducer are changed;
time measuring means for measuring, at each point scanned, a first period of time required for the ultrasonic wave transmitted by said first ultrasonic transducer to be received by said second ultrasonic transducer by passing through the object, as well as second and third periods of time respectively required for the ultrasonic wave transmitted by said third ultrasonic transducer to be received by said first and second ultrasonic transducers following scattering of the ultrasonic wave; and
propagation velocity distribution calculating means for finding propagation velocity of sound between mutually adjacent intersections of the rays at each point scanned in accordance with a predetermined sequence and based on the first, second and third periods of time concerning said mutually adjacent intersections, and for successively calculating a distribution of propagation velocity of sound in said plane interiorly of the object based on the propagation velocities of sound found.

10. The ultrasonic measurement apparatus according to claim 9, wherein the portion at which the rays intersect is made a focal region of said first, second and third ultrasonic transducers.

11. The ultrasonic measurement apparatus according to claim 9, wherein said scanning means include said first, second and third ultrasonic transducers, and circuitry for driving said transducers, wherein said first, second and third ultrasonic transducers each comprises a linear array of electronically scanned ultrasonic transducers.

* * * * *

UNITED STATES PATENT AND TRADEMARK OFFICE
CERTIFICATE OF CORRECTION

PATENT NO. : 4,625,555
DATED : December 2, 1986
INVENTOR(S) : Tadashi FUJII

It is certified that error appears in the above-identified patent and that said Letters Patent is hereby corrected as shown below:

COLUMN 10, line 42, "$x_{11}=Z_2-(T_{62}{}^8 \cdot c_0)/2$" should read --$x_{11}=Z_2-(T_{62}{}^{62} \cdot c_0)/2$--;

COLUMN 10, line 58, "$^{60}-T_{58}{}^{\square}{}_]$" should read --$^{60}-T_{58}{}^{58}{}_]$--;

COLUMN 14, line 23, "...we find $t'_{12}$..." should read --...we find $t'_{13}$...--.

Signed and Sealed this

Sixteenth Day of June, 1987

*Attest:*

DONALD J. QUIGG

*Attesting Officer*  *Commissioner of Patents and Trademarks*